US011996001B2

(12) United States Patent
Otsuki et al.

(10) Patent No.: US 11,996,001 B2
(45) Date of Patent: May 28, 2024

(54) MOTION SUPPORT SYSTEM, ACTION SUPPORT METHOD, PROGRAM, LEARNING APPARATUS, TRAINED MODEL, AND LEARNING METHOD

(71) Applicant: Toyota Jidosha Kabushiki Kaisha, Toyota (JP)

(72) Inventors: Nobuhisa Otsuki, Toyota (JP); Yoshiaki Kato, Miyoshi (JP); Issei Nakashima, Toyota (JP); Manabu Yamamoto, Toyota (JP); Hiroaki Daba, Nisshin (JP); Taiga Matsumoto, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 967 days.

(21) Appl. No.: 16/907,817

(22) Filed: Jun. 22, 2020

(65) Prior Publication Data
US 2021/0005106 A1    Jan. 7, 2021

(30) Foreign Application Priority Data
Jul. 1, 2019    (JP) .................................. 2019-123127

(51) Int. Cl.
*G09B 19/00*    (2006.01)
*A61H 1/02*    (2006.01)
(Continued)

(52) U.S. Cl.
CPC ......... *G09B 19/003* (2013.01); *A61H 1/0262* (2013.01); *G05B 13/0265* (2013.01);
(Continued)

(58) Field of Classification Search
CPC ................ G09B 19/003; A61H 1/0262; A61H 2201/501; A61H 2201/0173;
(Continued)

(56) References Cited

U.S. PATENT DOCUMENTS

2014/0058299 A1    2/2014    Sankai et al.
2019/0150792 A1*   5/2019    Nakashima .......... A61B 5/1128
2020/0384312 A1   12/2020    Nakashima et al.

FOREIGN PATENT DOCUMENTS

JP    2013-138793 A    7/2013
JP    2019-084644 A    6/2019
(Continued)

OTHER PUBLICATIONS

U.S. Appl. No. 16/875,422, filed May 15, 2020.

*Primary Examiner* — Joy Chng
(74) *Attorney, Agent, or Firm* — Dinsmore & Shohl LLP

(57) ABSTRACT

A walking training apparatus is a motion support system that includes a walking assistance apparatus as an assistance apparatus, a selected assistance level setting unit, a load data acquisition unit, an angle sensor as a displacement sensor, and an overall control unit as a control unit. The assistance apparatus assists a motion of a joint performed by a user. The assistance level setting unit sets an assistance level that is a level of a force exerted by the assistance apparatus. The load data acquisition unit acquires load data related to a load of the assistance apparatus. The displacement sensor detects a displacement of the joint. The control unit determines a recommended assistance level, which is an assistance level to be recommended, based on the assistance level, the load data, and an output of the displacement sensor, and outputs information about the determined recommended assistance level.

6 Claims, 17 Drawing Sheets

(51) Int. Cl.
  *G05B 13/02* (2006.01)
  *G16H 20/30* (2018.01)
(52) U.S. Cl.
  CPC ....... *G16H 20/30* (2018.01); *A61H 2201/501* (2013.01); *A63B 2220/24* (2013.01); *A63B 2220/833* (2013.01)
(58) Field of Classification Search
  CPC .... A61H 2201/0192; A61H 2201/1207; A61H 2201/163; A61H 2201/1635; A61H 2201/1642; A61H 2201/1652; A61H 2201/5043; A61H 2201/5061; A61H 2201/5069; A61H 2201/5084; A61H 2201/5092; A61H 2230/62; A61H 1/00; A61H 1/0237; A61H 1/024; A61H 3/008; A61H 3/00; A61H 2003/005; A61H 2201/5007; G05B 13/0265; G16H 20/30; A63B 2220/24; A63B 2220/833; A63B 22/025; G06N 3/08
  USPC .......................................................... 601/5
  See application file for complete search history.

(56) References Cited

FOREIGN PATENT DOCUMENTS

| | | | |
|---|---|---|---|
| JP | 2019-092603 A | 6/2019 | |
| JP | 2020-198996 A | 12/2020 | |
| WO | 2012/118143 A1 | 9/2012 | |
| WO | WO-2019116093 A1 * | 6/2019 | ............. A61H 1/024 |

\* cited by examiner

| DATA SET No. | PARAMETER 1 WALKING FIM | PARAMETER 2 WALKING FIM | PARAMETER 3 ANGLE | PARAMETER 4 LOAD DATA | TEACHER DATA ASSISTANCE LEVEL |
|---|---|---|---|---|---|
| 1 | 2 | 3 | DATA 13 | DATA 14 | 2 |
| 2 | 1 | 2 | DATA 23 | DATA 24 | 5 |
| 3 | 7 | 6 | DATA 33 | DATA 34 | 1 |
| ⋮ | ⋮ | ⋮ | ⋮ | ⋮ | ⋮ |

Fig. 15

MOTION SUPPORT SYSTEM, ACTION SUPPORT METHOD, PROGRAM, LEARNING APPARATUS, TRAINED MODEL, AND LEARNING METHOD

CROSS REFERENCE TO RELATED APPLICATIONS

This application is based upon and claims the benefit of priority from Japanese patent application No. 2019-123127, filed on Jul. 1, 2019, the disclosure of which is incorporated herein in its entirety by reference.

BACKGROUND

The present disclosure relates to a motion support system, a motion support method, a program, a learning apparatus, a trained model, and a learning method.

A use of a motion support system for supporting a motion of a user has become widespread. The motion support system may be used by a healthy person when he/she performs a predetermined task, or used by a trainee such as a patient suffering from paralysis as a rehabilitation support system when he/she performs rehabilitation. Such a motion support system assists the movement of the user's joint, regardless of whether the user is a healthy person or a trainee.

For example, the motion support system described in Japanese Unexamined Patent Application Publication No. 2013-138793 includes a link mechanism for rotatably supporting a joint, drive means for driving the link mechanism to assist a motion of the joint, angle detection means for detecting an angle of the joint, and control means for controlling the drive means based on the angle of the joint. The control means performs control so as to vary a driving torque of the driving means when it is determined that the angle of the joint is outside of a predetermined range based on the angle detected by the angle detection means.

Such a motion support system has a problem in appropriately setting an assistance level for a user. The assistance level here is the level of the assistance operation when the motion support system supports a motion of the user. When the assistance level is not properly set, the motion support system cannot perform an assistance operation suitable for the user.

The present disclosure has been made in order to solve such a problem. An object of the present disclosure is to provide a motion support system or the like for setting an appropriate assistance level.

An example aspect of the present disclosure is a motion support system including an assistance apparatus, an assistance level setting unit, a load data acquisition unit, a displacement sensor, and a control unit. The assistance apparatus assists a motion of a joint performed by a user. The assistance level setting unit is configured to set an assistance level that is a level of a force exerted by the assistance apparatus. The load data acquisition unit is configured to acquire load data related to a load of the assistance apparatus. The displacement sensor is configured to detect a displacement of the joint. The control unit is configured to determine a recommended assistance level, which is an assistance level to be recommended, based on the assistance level, the load data, and an output of the displacement sensor, and to output information about the determined recommended assistance level.

Thus, the motion support system can determine a recommended assistance level from the assistance level, the load data, and the output of the displacement sensor acquired from the motions performed by the user.

The above motion support system may further include a storage unit configured to store statistical data about a motion of the joint performed in the last. The statistical data is generated by collecting the assistance level, the load data, and the output of the displacement sensor. The control unit may be configured to determine the recommended assistance level based on the statistical data. Thus, the motion support system can appropriately determine the recommended assistance level using the statistical data.

The motion of the joint assisted by the above assistance apparatus may be included in rehabilitation performed by the user as a trainee, and the above motion support system may further include a storage unit configured to store statistical data about rehabilitation performed in the past. The statistical data is generated by collecting index data indicating a degree of recovery of the trainee, the assistance level, the load data, and the output of the displacement sensor. The control unit is configured to determine the recommended assistance level based on the statistical data and the index data of the trainee. Thus, the motion support system can appropriately determine the recommended assistance level in the rehabilitation using the statistical data.

In the above motion support system, the assistance apparatus may include a driving motor, and the load data acquisition unit may be configured to acquire information about power consumption of the driving motor. Thus, the motion support system can monitor the power consumption of the driving motor and acquire the load data.

In the above motion support system, the displacement sensor may be configured to detect an angle of the joint. Thus, the motion support system can determine an assistance level according to the angle of the joint.

In the above motion support system, the assistance apparatus may be configured to assist an extending motion and a flexing motion of a knee joint in a walking motion of the user. Further, the above motion support system may further include a walking cycle detection unit configured to detect a walking cycle of the walking motion. The control unit may be configured to determine the recommended assistance level based on the load data in a preset period included in a stance phase of the walking cycle and the output of the displacement sensor. Thus, the motion support system can appropriately assist the walking motion of the user.

Another example aspect of the present disclosure is a motion support method executed by a motion support system including an assistance apparatus for assisting a motion of a joint performed by a user. The motion support method includes an assistance level setting step, a load data acquisition step, a displacement detection step, a determination step, and an output step. The assistance level setting step is for setting an assistance level that is a level of a force exerted by the assistance apparatus. The load data acquisition step is for acquiring load data regarding a load of the assistance apparatus. The displacement detection step is for detecting a displacement of the joint. The determination step is for determining a recommended assistance level that is the assistance level to be recommended based on the assistance level, the load data, and the displacement. The output step is for outputting information about the recommended assistance level. Thus, the motion support method can determine a recommended assistance level from the assistance level, the load data, and the output of the displacement sensor acquired from the motions performed by the user.

Another example aspect of the present disclosure is a program for causing a computer to execute a motion support method executed by a motion support system including an assistance apparatus for assisting a motion of a joint performed by a user. The motion support method includes an assistance level setting step, a load data acquisition step, a displacement detection step, a determination step, and an output step. The assistance level setting step is for setting an assistance level that is a level of a force exerted by the assistance apparatus. The load data acquisition step is for acquiring load data regarding a load of the assistance apparatus. The displacement detection step is for detecting a displacement of the joint. The determination step is for determining a recommended assistance level that is the assistance level to be recommended based on the assistance level, the load data, and the displacement. The output step is for outputting information about the recommended assistance level. Thus, the program can determine a recommended assistance level from the assistance level, the load data, and the output of the displacement sensor acquired from the motions performed by the user.

Another example aspect of the present disclosure is a learning apparatus including a data acquisition unit and a learning unit. The data acquisition unit is configured to acquire a selected assistance level, load data, and displacement data as learning data. The selected assistance level is an assistance level indicating a level of a force exerted by the assistance apparatus selected from among a plurality of the assistance levels in regard to motion support executed by using a motion support system including an assistance apparatus for assisting a motion of a joint of a user. The load data is information related to a load of the assistance apparatus. The displacement data is related to a displacement of the joint. The learning unit is configured to learn to determine a recommended assistance level based on the learning data. The recommended assistance level is the assistance level of the assistance apparatus recommended for the user that should be selected when he/she uses the motion support system. The learning unit is also configured to generate a trained model based on the learning. The trained model receives the load data and the displacement data and outputs the recommended assistance level. Thus, the learning apparatus can generate a trained model that outputs the recommended assistance level from the acquired load data and displacement data.

In the above learning apparatus, the learning unit may be configured to receive the load data and the displacement data and to perform the learning by using the selected assistance level as teacher data. Thus, the learning apparatus can perform supervised learning using the selected assistance level as the teacher data.

Another example aspect of the present disclosure may be a trained model configured to cause a computer to output the recommended assistance level based on the load data and the displacement data acquired from the assistance apparatus. By using this trained model, the recommended assistance level can be appropriately output for untrained input data.

Another example aspect of the present disclosure may be a motion support system capable of accessing a trained model that is a learning model generated by the above learning apparatus. The motion support system includes: an output unit configured to output the load data and the displacement data as an input to the trained model; and a notification unit configured to notify the user of the motion support system of the recommended assistance level output from the trained model as a response to the input load data and the input displacement data. Thus, the motion support system can appropriately notify the user of the recommended assistance level.

Another example aspect of the present disclosure is a learning method including a data acquisition step, a learning step, and a trained model generation step. The data acquisition step is for acquiring a selected assistance level, load data, and displacement data as learning data. The selected assistance level is an assistance level indicating a level of a force exerted by the assistance apparatus selected from among a plurality of the assistance levels in regard to motion support executed by using a motion support system including an assistance apparatus for assisting a motion of a joint of a user. The load data is related to a load of the assistance apparatus. The displacement data is related to a displacement of the joint. The learning step is for learning to determine a recommended assistance level based on the learning data. The recommended assistance level is the assistance level of the assistance apparatus recommended for the user that should be selected when he/she uses the motion support system. The trained model generation step is for generating a trained model based on the learning. The trained model receives the load data and the displacement data and outputs the recommended assistance level. Thus, the learning method can generate a trained model that outputs a recommended assistance level from the acquired load data and displacement data.

According to the present disclosure, it is possible to provide a motion support system or the like for setting an appropriate assistance level.

The above and other objects, features and advantages of the present disclosure will become more fully understood from the detailed description given hereinbelow and the accompanying drawings which are given by way of illustration only, and thus are not to be considered as limiting the present disclosure.

BRIEF DESCRIPTION OF DRAWINGS

FIG. 15 shows an example of data input to the learning apparatus.

DETAILED DESCRIPTION

Hereinafter, the present disclosure will be explained through embodiments of the present disclosure. However, they are not intended to limit the scope of the present disclosure according to the claims. Note that the same elements are denoted by the same reference signs throughout the drawings, and repeated description is omitted as necessary. Note that the same elements are denoted by the same reference signs throughout the drawings, and repeated description is omitted as necessary.

First Embodiment

Figure 1:
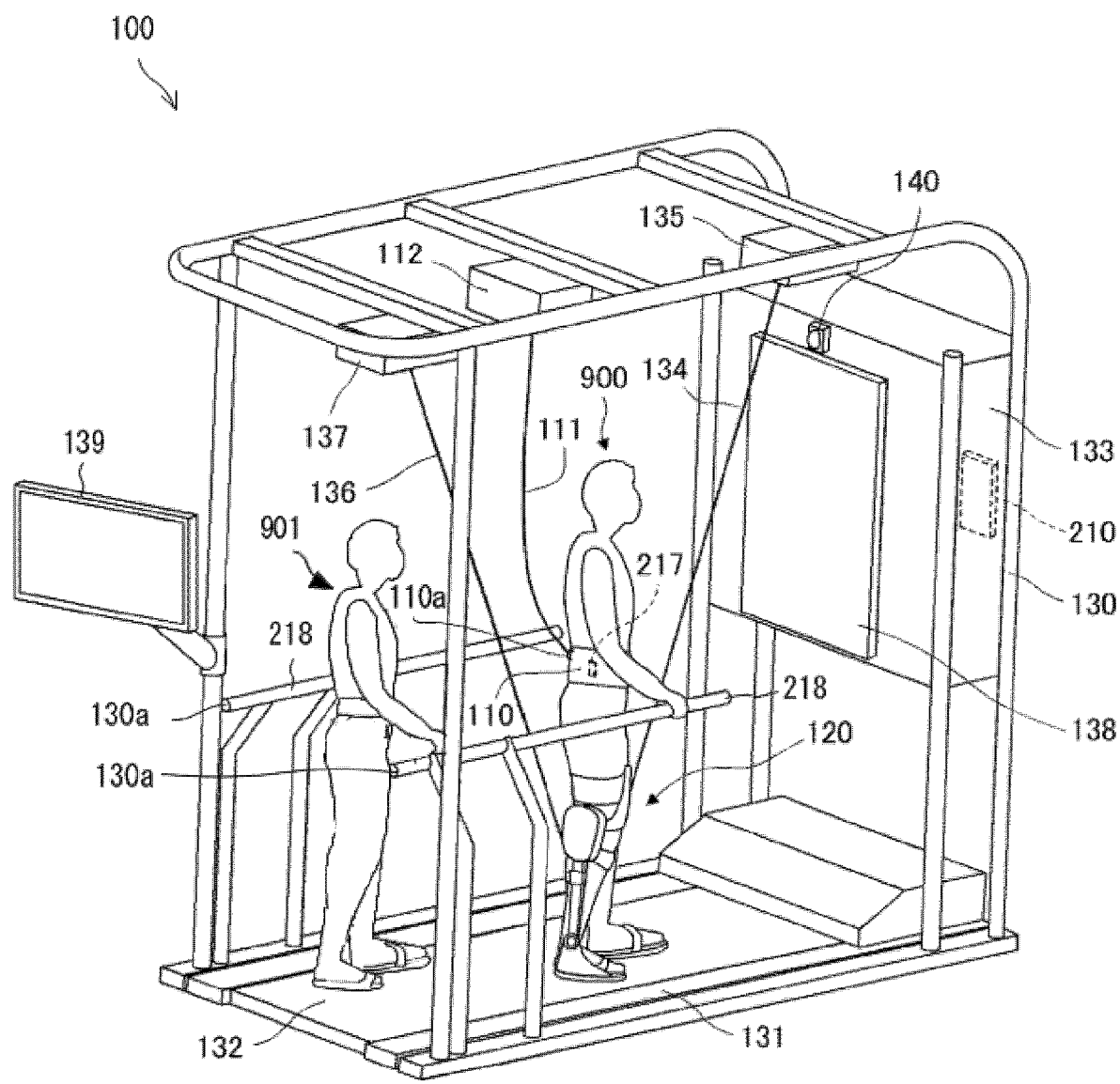
FIG. 1 is a schematic perspective view of a walking training apparatus according to a first embodiment.

A first embodiment will be described hereinafter with reference to the drawings.
(System Configuration)
FIG. 1 is a schematic perspective view of a walking training apparatus 100 according to a first embodiment. The walking training apparatus 100 is an embodiment of a motion support system for supporting a motion of a user. More specifically, the walking training apparatus 100 is a specific example of a rehabilitation support apparatus that supports rehabilitation performed by a trainee 900 who is a user. The walking training apparatus 100 is an apparatus by which the trainee 900, who is, for example, a hemiplegic patient suffering from paralysis in one of his/her legs, does walking training under the guidance of a training staff member 901. Note that the training staff member 901 can be a therapist (a physical therapist) or a doctor, and may also be referred to as a training instructor, a training assistant, a training supporter, or the like because he/she instructs the trainee in training or assists the trainee by giving assistance and the like.

The walking training apparatus 100 mainly includes a control panel 133 attached to a frame 130 forming an overall framework, a treadmill 131 on which the trainee 900 walks, and a walking assistance apparatus 120 attached to the diseased leg, i.e., the leg on the paralyzed side of the trainee 900.

The frame 130 is disposed in a standing position on the treadmill 131 mounted on the floor surface. The treadmill 131 rotates a ring-shaped belt 132 by using a motor (not shown). The treadmill 131 is an apparatus that prompts the trainee 900 to walk, and the trainee 900, who does a walking training, gets on the belt 132 and tries walking in accordance with the movement of the belt 132. Note that the training staff member 901 can stand on the belt 132 behind the trainee 900 and walk together as shown in FIG. 1. However, the training staff member 901 may typically be in a state in which he/she can easily assists the trainee 900 such as standing with his/her feet on both sides of the belt 132.

The frame 130 supports, for example, the control panel 133 that houses an overall control unit 210 that controls motors and sensors, and a training monitor 138 that is formed by, for example, a liquid-crystal panel and shows progress of the training and the like to the trainee 900. Further, the frame 130 supports a front pulling unit 135 roughly above and in front of the head of the trainee 900, supports a harness pulling unit 112 roughly above the head, and supports a rear pulling unit 137 roughly above and behind the head. Further, the frame 130 also includes handrails 130a that the trainee 900 grasps.

The handrails 130a are disposed on the left and right sides of the trainee 900. Each of the handrails 130a is orientated in a direction parallel to the walking direction of the trainee 900. The vertical position and the left/right position of the handrails 130a are adjustable. That is, the handrails 130a may include a mechanism for changing its height. Further, the handrails 130a can be configured so that their inclination angles can be changed by, for example, adjusting the heights of their front sides and the rear sides in the walking direction to different heights. For example, the handrails 130a can have an inclination angle so that their heights gradually increase along the walking direction.

Further, each of the handrails 130a is equipped with a handrail sensor 218 that detects a load (e.g., a pressure) received from the trainee 900. For example, the handrail sensor 218 may be a resistance change detection-type load detection sheet in which electrodes are arranged in a matrix pattern. Further, the handrail sensor 218 may be a six-axis sensor in which a three-axis acceleration sensor (x, y, z) is combined with a three-axis gyro sensor (roll, pitch, yaw). However, there is no particular limitation on the type of the handrail sensor 218 and the place where the handrail sensor 218 is disposed.

The camera 140 functions as an image pickup unit for observing the whole body of the trainee 900. The camera 140 is disposed near the training monitor 138 and positioned so as to face the trainee. The camera 140 takes still images and moving images of the trainee 900 during the training. The camera 140 includes a set of a lens and an image pickup device so that it has such an angle of view that it can shoot the whole body of the trainee 900. The image pickup device is, for example, a CMOS (Complementary Metal-Oxide-Semiconductor) image sensor, and converts an optical image formed on an image forming surface into an image signal.

By the coordinated operation of the front pulling unit 135 and the rear pulling unit 137, the load of the walking assistance apparatus 120 is canceled so that it does not become a load on the diseased leg. Further, the swinging motion of the diseased leg is assisted according to the set level.

One end of a front wire 134 is connected to a winding mechanism of the front pulling unit 135 and the other end thereof is connected to the walking assistance apparatus 120. The winding mechanism of the front pulling unit 135 winds or pays out the front wire 134 according to the motion of the diseased leg by turning on/off a motor (not shown). Similarly, one end of a rear wire 136 is connected to the winding mechanism of the rear pulling unit 137 and the other end thereof is connected to the walking assistance apparatus 120. The winding mechanism of the rear pulling unit 137 winds or pays out the rear wire 136 according to the motion of the diseased leg by turning on/off a motor (not shown). By the coordinated operation of the front pulling unit 135 and the rear pulling unit 137 as described above, the load of the walking assistance apparatus 120 is canceled so that it does not become a load on the diseased leg. Further, the swinging motion of the diseased leg is assisted according to the set level.

For example, the training staff member 901, who serves as an operator, increases the set assistance level for a trainee who suffers from severe paralysis. When the assistance level is set to a large value, the front pulling unit 135 winds the front wire 134 with a relatively large force according to the timing of the swinging of the diseased leg. When the training has progressed and the assistance is no longer required, the training staff member 901 sets the assistance level to the minimum value. When the assistance level is set to the minimum value, the front pulling unit 135 winds the front wire 134 according to the timing of the swinging of the diseased leg with a force by which only the weight of the walking assistance apparatus 120 itself is canceled.

The walking training apparatus 100 includes a fall-prevention harness apparatus as a safety apparatus, which includes, as its main components, a harness 110, a harness wire 111, and a harness pulling unit 112. The harness 110 is a belt that is wound around the abdomen of the trainee 900 and is fixed to his/her waist by, for example, a hook-and-loop fastener. The harness 110 includes a connection hook 110a that connects one end of the harness wire 111, which serves as a hoisting tool, to the harness 110, and may be referred to as a hanger belt. The trainee 900 attaches the harness 110 to his/her diseased leg so that the connection hook 110a is positioned in the rear part of the diseased leg.

One end of the harness wire 111 is connected to the connection hook 110a of the harness 110 and the other end thereof is connected to a winding mechanism of the harness pulling unit 112. The winding mechanism of the harness pulling unit 112 winds or pays out the harness wire 111 by turning on/off a motor (not shown). By the above-described configuration, when the trainee 900 is about to fall down, the fall-prevention harness apparatus winds the harness wire 111 according to an instruction from the overall control unit 210, which has detected the falling-down movement of the trainee 900, and thereby supports the upper body of the trainee 900 by the harness 110, so that the trainee 900 is prevented from falling down.

The harness 110 includes a posture sensor 217 for detecting the posture of trainee 900. The posture sensor 217 is, for example, a combination of a gyro sensor and an acceleration sensor, and outputs an inclination angle of the abdomen, to which the harness 110 is attached, with respect to the direction of gravity.

A management monitor 139 is attached to the frame 130 and serves as a display/input device by which the training staff member 901 or the like monitors and operates the rehabilitation support system. The management monitor 139 is formed by, for example, a liquid crystal panel. Further, a touch panel is disposed over its surface. The management monitor 139 displays various menu items related to the training setting, various parameter values during the training, training results, and so on.

The walking assistance apparatus 120 is attached to the diseased leg of the trainee 900 and assists the trainee 900 in walking by reducing the load of the extension and flexion at the knee joint of the diseased leg. The walking assistance apparatus 120 includes a sensor or the like that measures the load (e.g., the pressure) on the sole of the foot, and outputs various data related to the moving leg to the overall control unit 210. Further, the harness 110 can be connected to the walking assistance apparatus 120 by using a connection member (hereinafter referred to as a hip joint) including a rotation part. Details of the walking assistance apparatus 120 will be described later.

In this embodiment, the terms "leg" and "leg part" are used to refer to the entire part of the leg below the hip joint, and the terms "foot" and "foot part" are used to refer to a part of the leg from the ankle to the toe.

In the first embodiment, the walking training apparatus 100 is described as an example of the motion support system, but the motion support system is not limited to this. For example, the motion support system may be arbitrary rehabilitation support system or rehabilitation support system for supporting rehabilitation of a trainee. For example, the rehabilitation support system may be an upper-limb rehabilitation support system that supports rehabilitation of a shoulder(s) or an arm(s). Alternatively, the rehabilitation support system may be a rehabilitation support system that supports rehabilitation for a balancing ability of a trainee. The motion support system is not limited to the above-described rehabilitation support system, and instead may be the one worn and used when a healthy person who is a user performs a predetermined motion such as light work, or used by a healthy person who is a user to train a predetermined body part.

Figure 2:
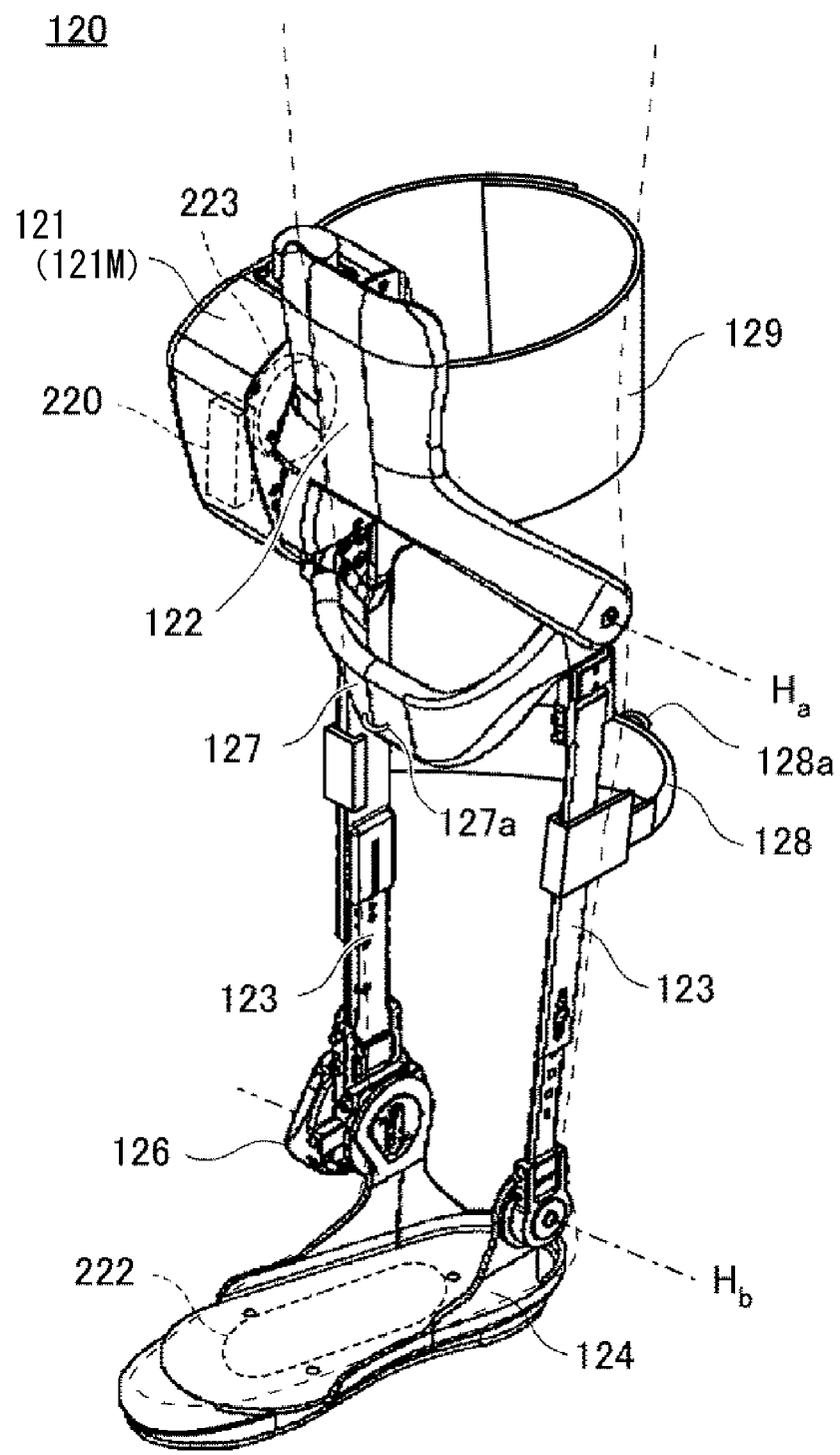
FIG. 2 is a schematic perspective view of the walking assistance apparatus.

Next, the walking assistance apparatus 120 will be described with reference to FIG. 2. FIG. 2 is a schematic perspective view showing an example of a configuration of the walking assistance apparatus 120. The walking assistance apparatus 120 mainly includes a control unit 121, a plurality of frames that support each part of a diseased leg, and a load sensor 222 for detecting a load (e.g., a pressure) applied to the sole.

The control unit 121 includes an assistance control unit 220 that controls the walking assistance apparatus 120, and also includes a motor(s) (not shown) that generates a driving force(s) for assisting extending movements and flexing movements of the knee joint. The frames, which support each part of the diseased leg, includes an upper-leg frame 122 and a lower-leg frame 123 rotatably connected to the upper-leg frame 122. Further, the frames also include a sole frame 124 rotatably connected to the lower-leg frame 123, a front connection frame 127 for connecting a front wire 134, and a rear connection frame 128 for connecting a rear wire 136.

The upper-leg frame 122 and the lower-leg frame 123 rotate relative to each other around a hinge axis $H_a$ shown in the figure. A motor 121M of the control unit 121 is a driving motor that rotates according to an instruction from the assistance control unit 220, and by doing so, force the upper-leg frame 122 and the lower-leg frame 123 to open relative to each other around the hinge axis $H_a$ or force them to close relative to each other. The angle sensor 223 housed in the control unit 121 is, for example, a rotary encoder and detects an angle between the upper-leg frame 122 and the lower-leg frame 123 around the hinge axis $H_a$. The lower-leg frame 123 and the sole frame 124 rotate relative to each other around a hinge axis $H_b$ shown in the figure. The angular range of their relative rotation is adjusted in advance by an adjustment mechanism 126.

The front connection frame 127 is disposed so as to extend in the left/right direction in front of the upper leg and is connected to the upper-leg frame 122 at both ends. Further, a connection hook 127a for connecting the front wire 134 is provided at or near the center of the front connection frame 127 in the left/right direction. The rear connection frame 128 is disposed so as to extend in the left/right direction behind the lower leg and is connected to the lower-leg frame 123 at both ends. Further, a connection hook 128a for connecting the rear wire 136 is provided at or near the center of the rear connection frame 128 in the left/right direction.

The upper-leg frame 122 includes an upper-leg belt 129. The upper-leg belt 129 is a belt integrally provided in the upper-leg frame and is wound around the upper leg of the diseased leg to fix the upper-leg frame 122 to the upper leg. In this way, the whole walking assistance apparatus 120 is prevented from being displaced from the leg of the trainee 900.

The load sensor 222 is a load sensor embedded in the sole frame 124. The load sensor 222 may be configured to detect a magnitude and a distribution of a vertical load (e.g., a vertical pressure) received by the sole of the trainee 900. For example, the load sensor 222 may be configured to detect a COP (Center Of Pressure) of the sole. The load sensor 222 is, for example, a resistance change detection-type load detection sheet in which electrodes are arranged in a matrix pattern.

Figure 3:
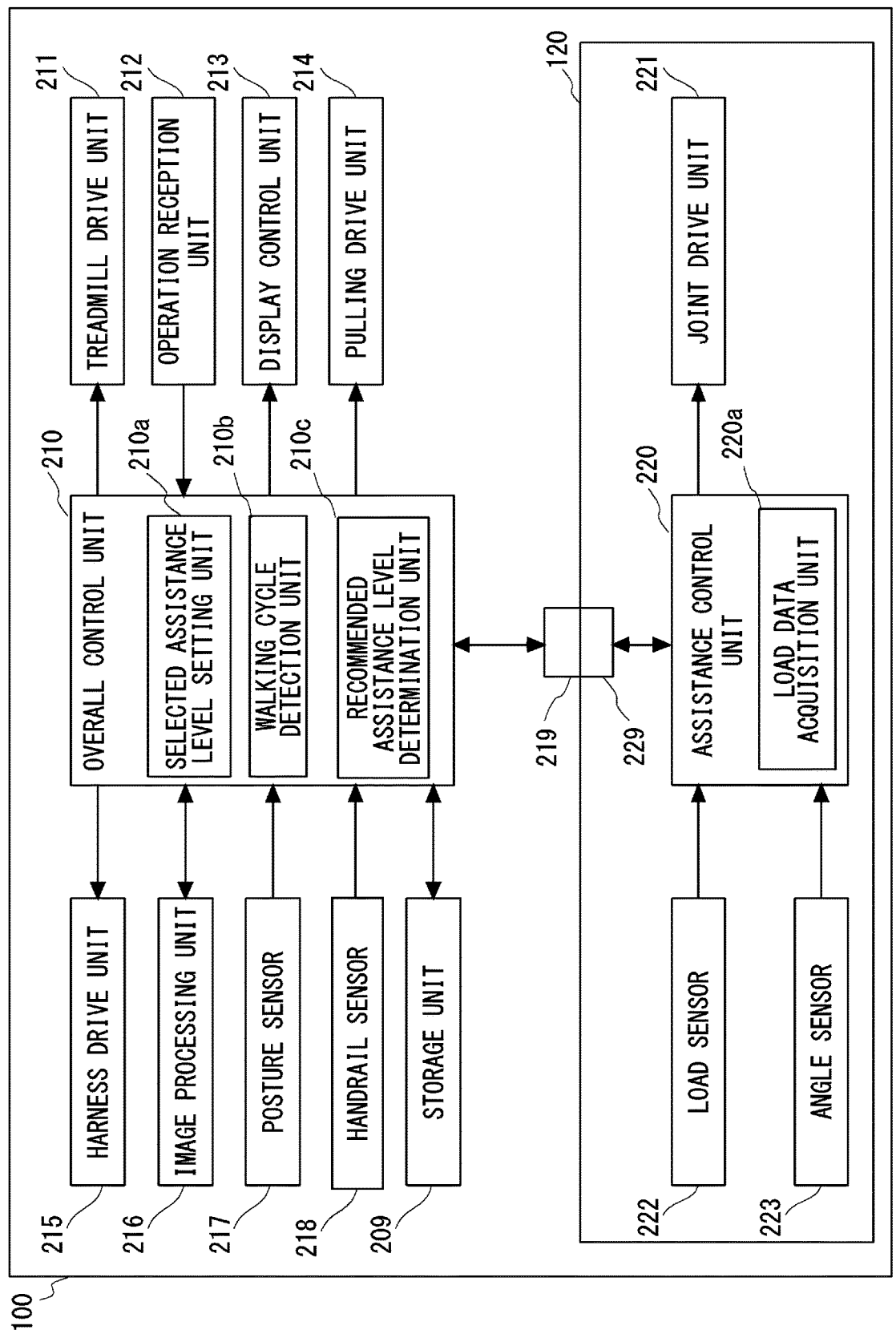
FIG. 3 is a block diagram showing a system configuration of the walking training apparatus.

Next, an example of a system configuration of the walking training apparatus 100 will be described with reference to FIG. 3. FIG. 3 is a block diagram showing an example of a system configuration of the walking training apparatus 100. As shown in FIG. 3, the walking training apparatus 100 may include an overall control unit 210, a treadmill drive unit 211, an operation reception unit 212, a display control unit 213, and a pulling drive unit 214. Further, the walking training apparatus 100 may include a harness drive unit 215, an image processing unit 216, a posture sensor 217, a handrail sensor 218, a communication connection IF (interface) 219, an input and output unit 231, and a walking assistance apparatus 120.

The overall control unit 210 is, for example, an MPU (Micro Processing Unit) and controls the overall operations of the apparatus by executing a control program loaded from a system memory. The overall control unit 210 evaluates whether the walking motion of the trainee 900 is abnormal or not by using, for example, data acquired from various sensors. The overall control unit 210 determines a training result of a series of walking trainings based on, for example, a cumulative number of the abnormal walking. The overall control unit 210 can generate, as part of the rehabilitation data, a result of this determination or the cumulative number of the abnormal walking, based on which the determination result has been obtained. The overall control unit 210 includes a selected assistance level setting unit 210a, a walking cycle detection unit 210b, and a recommended assistance level determination unit 210c.

The selected assistance level setting unit 210a sets an assistance level of the walking training to be executed. The selected assistance level is an assistance level actually set in the walking training. The selected assistance level is set to an assistance level determined by a training staff member such as a PT. More specifically, the selected assistance level setting unit 210a receives an instruction to set the selected assistance level through the operation reception unit 212. The selected assistance level setting unit 210a, which has received the instruction, instructs the walking assistance apparatus 120 to operate at the set selected assistance level. The selected assistance level is appropriately changed by an operation received from the PT or the like.

The walking cycle detection unit 210b detects a walking cycle of a trainee 900 under training. The walking cycle detection unit 210b determines, for example, whether the sole of the diseased leg is in contact with the treadmill 131, or whether it is a stance phase in which the sole is in contact with the treadmill 131 or in a swing phase in which the sole is not in contact with the treadmill 131, from data acquired from the load sensor 222 of the walking assistance apparatus 120. The walking cycle detection unit 210b detects a walking pattern of the trainee 900. The details of the walking cycle will be described later. The walking cycle detection unit 210b may recognize the trainee from an image of the trainee 900's body captured by the camera 140 in place of the data acquired from the load sensor 222, and detect a walking pattern from the recognized image of the trainee 900. The walking cycle detection unit 210b may detect a walking pattern from data generated by the load sensor 222 or the angle sensor 223 included in the walking assistance apparatus 120, instead of using the above-described means.

The recommended assistance level determination unit 210c acquires load data and displacement data from the walking assistance apparatus 120, reads reference data stored in the storage unit 209, and determines an assistance level to be recommended (recommended assistance level). For example, the load data may be power consumption or current consumption of the motor 121M. When the control unit 121 includes a torque sensor (not shown), the load data may be an output of the torque sensor. The displacement data is an output of the angle sensor 223. The recommended assistance level determination unit 210c may read the statistical data stored in the storage unit 209 and determine the recommended assistance level from the read statistical data.

Note that the statistical data is generated by collecting an assistance level, load data, and an output of the displacement sensor for the training performed in the past. The overall control unit 210 generates such statistical data, and stores the generated statistical data in the storage unit 209.

The treadmill drive unit 211 includes a motor that rotates the belt 132 and its drive circuit. The overall control unit 210 controls the rotation of the belt 132 by sending a drive signal to the treadmill drive unit 211. The overall control unit 210 adjusts, for example, the rotational speed of the belt 132 according to a walking speed set by the training staff member 901.

The operation reception unit 212 receives an input operation from the training staff member 901 and transmits an operation signal to the overall control unit 210. The training staff member 901 operates operation buttons provided in the apparatus, a touch panel disposed over the management monitor 139, an accessory remote controller, etc., which constitute the operation reception unit 212. By the above-described operation, the training staff member can turn on/off the power, provide an instruction to start training, enter a numerical value for the setting, and select a menu item. Note that the operation reception unit 212 can also receive an input operation from the trainee 900.

The display control unit 213 receives a display signal from the overall control unit 210, generates a display image, and displays the generated display image on the training monitor 138 or the management monitor 139. The display control unit 213 generates an image showing progress of the training and a real-time video image shot by the camera 140.

The pulling drive unit 214 includes a motor for pulling the front wire 134 and its drive circuit, which constitute the front pulling unit 135, and a motor for pulling the rear wire 136 and its drive circuit, which constitute the rear pulling unit 137. The overall control unit 210 controls winding of the front wire 134 and winding of the rear wire 136 by sending a drive signal(s) to the pulling drive unit 214. Further, the pulling force of each wire is controlled by controlling the driving torque of the respective motor in addition to controlling the winding operation. The overall control unit 210 identifies (i.e., determines), for example, a timing at which the diseased leg changes from a stance state to a swing state from the result of the detection by the load sensor 222, and assists the swinging action of the diseased leg by increasing or decreasing the pulling force of each wire in synchronization with the identified timing.

The harness drive unit 215 includes a motor for pulling the harness wire 111 and its drive circuit, which constitute the harness pulling unit 112. The overall control unit 210 controls winding of the harness wire 111 and the pulling force of the harness wire 111 by sending a drive signal(s) to the harness drive unit 215. For example, when the overall control unit 210 predicts that the trainee 900 will fall down, it prevents the trainee from falling down by winding the harness wire 111 by a certain length.

The image processing unit 216 is connected to the camera 140, so that it can receive an image signal from the camera 140. The image processing unit 216 receives an image signal from the camera 140 according to an instruction from the overall control unit 210, and generates image data by performing image processing on the received image signal. Further, the image processing unit 216 can also perform a specific image analysis by performing image processing on the image signal received from the camera 140 according to an instruction from the overall control unit 210. For example, the image processing unit 216 detects the position of the foot of the diseased leg at which the foot is in contact with the treadmill 131 (i.e., a stance position) by the image analysis. Specifically, for example, the image processing unit 216 extracts an image area near the tip of the sole frame 124, and calculates the stance position by analyzing an identification marker drawn on a part of the belt 132 where the tip of the sole frame 124 is located.

The posture sensor 217 detects an inclination angle of the abdomen of the trainee 900 with respect to the direction of gravity as described above, and transmits a detection signal to the overall control unit 210. The overall control unit 210 calculates the posture of the trainee 900, in particular, an inclination angle of his/her trunk by using the detection signal from the posture sensor 217. Note that the overall control unit 210 and the posture sensor 217 may be connected to each other through a cable or through short-range wireless communication.

The handrail sensor 218 detects a load (e.g., a pressure) applied to the handrail 130a. That is, the amount of the load corresponding to the part of the trainee's own weight that the trainee 900 cannot support by both legs is applied to the handrails 130a. The handrail sensor 218 detects this load and transmits a detection signal to the overall control unit 210.

The storage unit 209 is a storage device including a non-volatile memory such as a flash memory, an SSD (Solid State Drive), or an HDD (Hard Disc Drive), and previously stores the reference data used for determining a recommended assistance level. Details of the recommended assistance level and the assistance level will be described later. The storage unit 209 may store the statistical data generated by collecting the assistance level, the load data, and the output of the displacement sensor.

The communication connection IF 219 is an interface connected to the overall control unit 210, and is an interface for providing an instruction to the walking assistance apparatus 120 attached to the diseased leg of the trainee 900 and receiving sensor information therefrom.

The walking assistance apparatus 120 may include a communication connection IF 229 that is connected to the communication connection IF 219 through a cable or wirelessly. The communication connection IF 229 is connected to the assistance control unit 220 of the walking assistance apparatus 120. The communication connection IFs 219 and 229 are communication interfaces in conformity with communication standards, such as those of a wired LAN or a wireless LAN.

Further, the walking assistance apparatus 120 may include an assistance control unit 220, a joint drive unit 221, a load sensor 222, and an angle sensor 223. The assistance control unit 220 is, for example, an MPU and controls the walking assistance apparatus 120 by executing a control program supplied from the overall control unit 210. Further, the overall control unit 210 notifies the overall control unit 220 of the state of the walking assistance apparatus 120 through the communication connection IFs 229 and 219. Further, the assistance control unit 220 performs control of walking assistance apparatus 120, such as the start/stop thereof, in response to a command from the overall control unit 210. The assistance control unit 220 includes a load data acquisition unit 220a. The load data acquisition unit 220a acquires data (load data) related to the load of the walking assistance apparatus 120, and supplies the acquired load data to the overall control unit 210.

The joint drive unit 221 includes the motor 121M of the control unit 121 and its drive circuit. The assistance control unit 220 sends a drive signal to the joint drive unit 221 to force the upper-leg frame 122 and the lower-leg frame 123 to open relative to each other around the hinge axis $H_a$ or force them to close relative to each other. Through the above-described operations, the assistance control unit 220 assists an extending motion and a flexing motion of the knee and prevents the knee from buckling.

The joint drive unit 221 can switch a driving force of the motor 121M of the control unit 121 to preset levels. The switching of the driving force of the motor 121M in the control unit 121 is set as an assistance level. That is, the assistance level in this embodiment indicates the strength of an assistance operation performed for the trainee 900 performing walking training. Details of the assistance level will be described later.

The load sensor 222 detects the magnitude and the distribution of the vertical load (e.g., the vertical pressure) applied to the sole of the trainee 900 and transmits a detection signal to the assistance control unit 220 as described above. The assistance control unit 220 can receive and analyze the detection signal, and thereby determines the swing/stance state.

The angle sensor 223 detects the angle between the upper-leg frame 122 and the lower-leg frame 123 around the hinge axis $H_a$ and transmits a detection signal to the assistance control unit 220 as described above. The assistance control unit 220 receives this detection signal and calculates the open angle of the knee joint.

(Assistance Level)

Next, the assistance level in this embodiment will be described in detail. In the walking training apparatus 100 according to this embodiment, when the trainee 900 performs a walking training, the walking assistance apparatus 120 assists the trainee to walk. More specifically, the walking assistance apparatus 120 assists an extending motion and a flexing motion of the knee of the diseased leg according to a walking cycle of the trainee.

Figure 4:
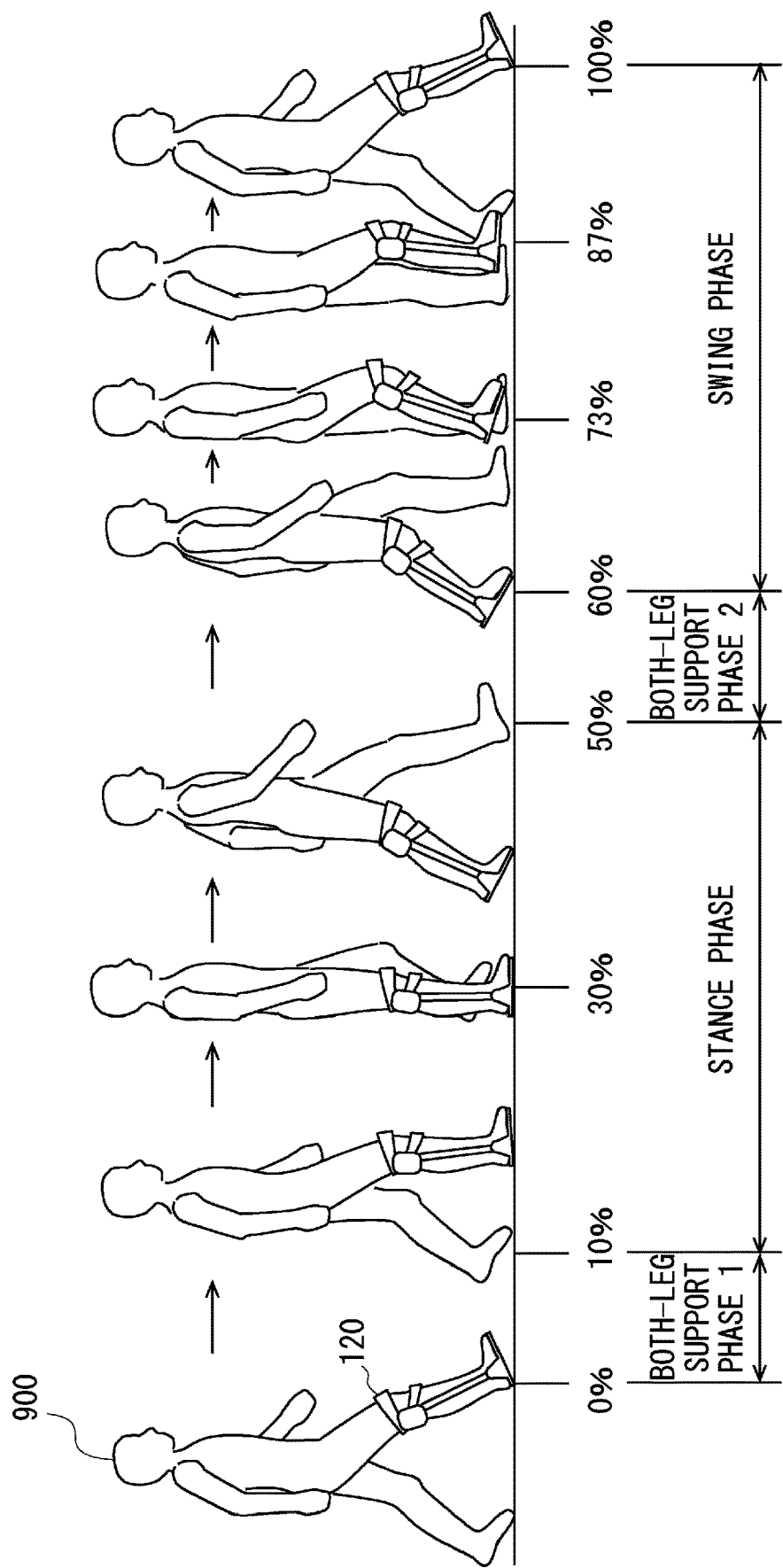
FIG. 4 shows an example of a walking cycle of a trainee.

The walking cycle of the trainee 900 will be described with reference to FIG. 4. FIG. 4 shows an example of the walking cycle of the trainee. FIG. 4 shows a walking trajectory for one cycle focusing on the right leg, which is the diseased leg of the trainee 900 walking from left to right. The walking trajectory is shown as 0% at a position where the right leg comes into contact with the floor surface, and 100% at a position where the right leg has walked for one cycle.

A walking cycle of one cycle is classified into 0 to 10% both-leg support phase 1, 10 to 50% stance phase, 50 to 60% both-leg support phase 2, and 60 to 100% swing phase. The both-leg support phase 1 is an initial stance phase, and the left leg, which is the leg opposite to the right leg, is also in contact with the floor surface. In the stance phase, the right leg (diseased leg), which is the leg of interest, comes into contact with the floor surface, and the left leg, which is the leg opposite to the right leg, is away from the floor surface. The both-leg support phase 2 is a terminal stance phase, and the left leg, which is the leg opposite to the right leg, also comes into contact with the floor surface. In the swing phase, the right leg, which is the leg of interest, is away from the floor surface.

The trainee 900 suffering from paralysis in the right leg may have difficulty supporting his/her weight during the stance phase of the walking cycle shown in the drawing. In such a case, the trainee 900's knee may greatly bend, resulting in "knee buckling". The knee buckling refers to a state in which, as the knee extension function deteriorates, the knee bends, and the trainee 900 cannot maintain the extending of his/her knee, and thus he/she unconsciously bends his/her knee while walking. Further, although the trainee 900 needs to extend his/her knee at the position around 30% of the walking cycle, he/she may not be able to extend his/her knee after bending his/her knee. Thus, the motor 121M of the control unit 121 is driven so as to prevent the knee from excessively bending or assist the knee to extend at a predetermined timing during the stance phase.

Figure 5:
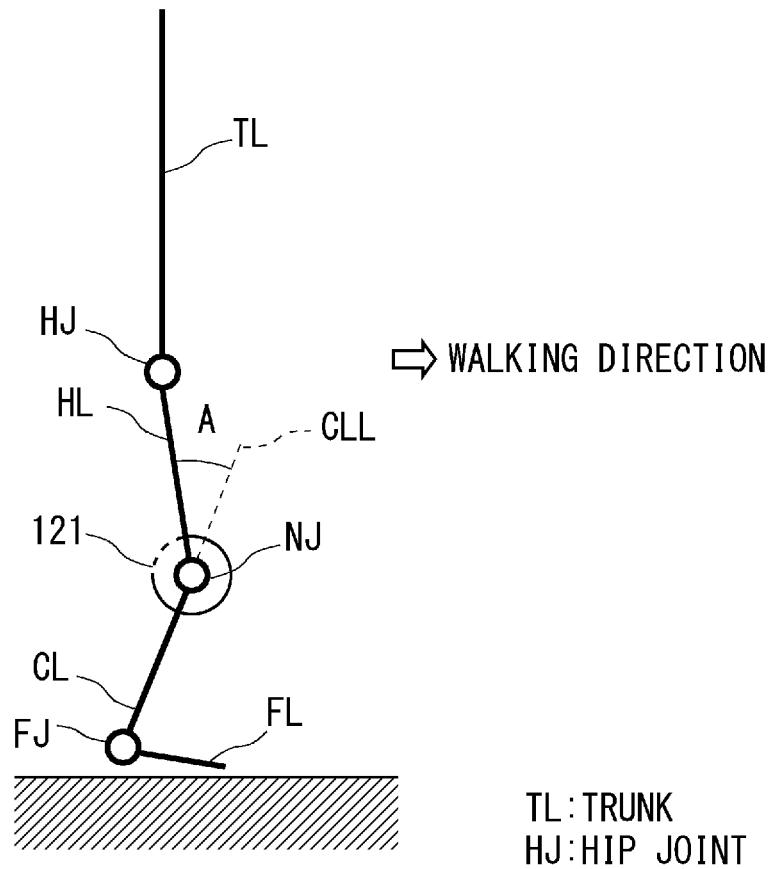
FIG. 5 shows an example of a knee extension angle of a diseased leg.

Next, an angle of the knee joint will be described with reference to FIG. 5. FIG. 5 shows an example of a knee extension angle of the diseased leg. FIG. 5 is a schematic diagram when the paralyzed body part, which is the lower body of the diseased leg, is observed from the side with respect to the walking direction. FIG. 5 shows a trunk TL, a hip joint HJ, an upper leg HL, a knee joint NJ, a lower leg CL, an ankle joint FJ, and a foot FL in order from the top. A lower leg extension line CLL is indicated by a dotted line as an extension line extending the lower leg CL upward. An angle between the upper leg HL and the lower-leg extension line CLL is shown as a knee extension angle A. In the schematic diagram of FIG. 5, the diseased leg of the trainee 900 is in the stance phase and is in contact with the floor surface.

The knee extension angle A of a healthy subject in the stance phase shown in the drawing is 10 to 15 degrees. Thus, the maximum knee extension angle A in the stance phase may be about 10 to 15 degrees even for the trainee 900 when he/she walks. However, when the trainee 900 cannot support his/her weight, the knee extension angle A may become much greater than 15. Thus, the motor 121M of the control unit 121 attached to the knee joint NJ is driven in a direction to return the knee extension angle A to within a predetermined range when the knee extension angle A exceeds a preset value.

Figure 6:
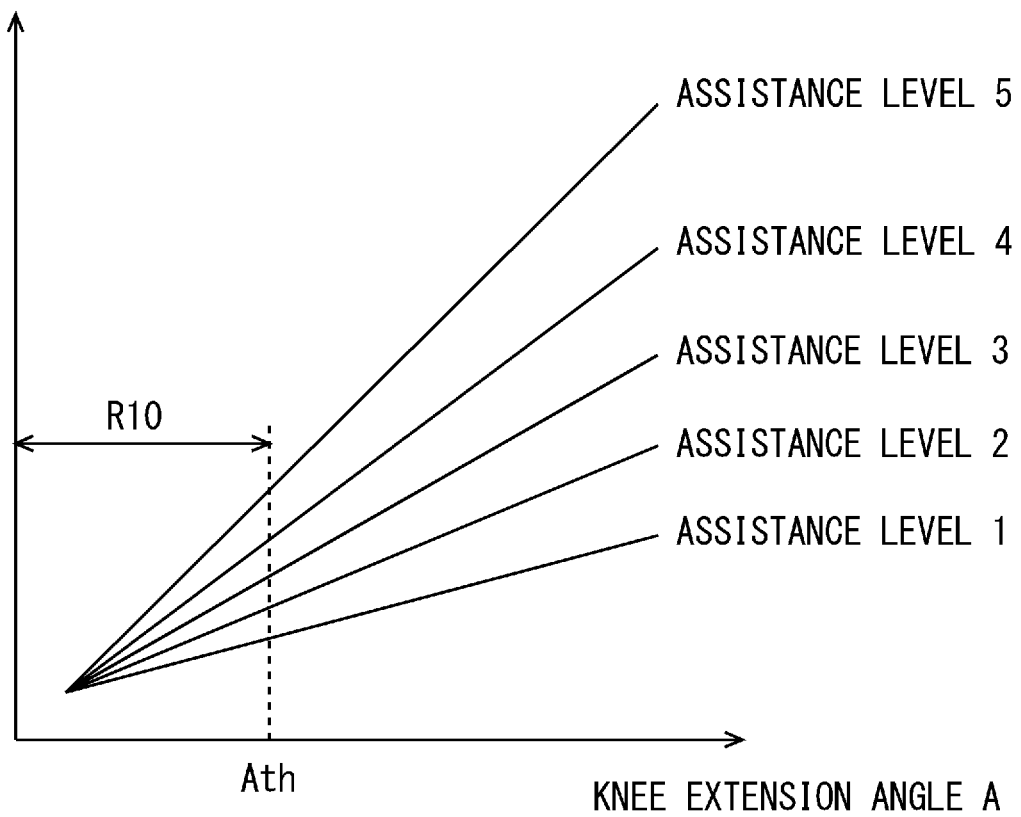
FIG. 6 is a first diagram showing an example of an assistance level.

Next, a relationship between the knee extension angle A and the torque of the motor 121M will be described with reference to FIG. 6. FIG. 6 is a first diagram showing an example of the assistance level. In the graph shown in the FIG. 6, the horizontal axis represents the knee extension angle A, and the vertical axis represents a torque T of the motor 121M. Solid straight lines plotted in the drawing indicate the assistance levels set in the motor 121M. In this embodiment, the assistance level is divided into 5 stages of 1 to 5.

The assistance levels are set such that the motor torque T increases as the knee extension angle A increases. In the example shown in this embodiment, the value of the motor torque T for the predetermined knee extension angle is the weakest at the assistance level 1 and the highest at the assistance level 5. Thus, the training staff member selects the assistance level 5, for example, for a trainee who needs strong assistance. The training staff member appropriately changes the assistance level according to the degree of recovery of the trainee.

A threshold Ath indicated by a dotted line in the drawing is set in the control unit 121. The threshold Ath is a threshold at which the motor 121M starts driving. That is, when the knee extension angle A exceeds the threshold Ath during the stance phase of the walking training, the motor 121M is driven to assist the knee extension operation. The motor torque T at the start of assisting the knee extension operation is determined by the set assistance level.

Figure 7:
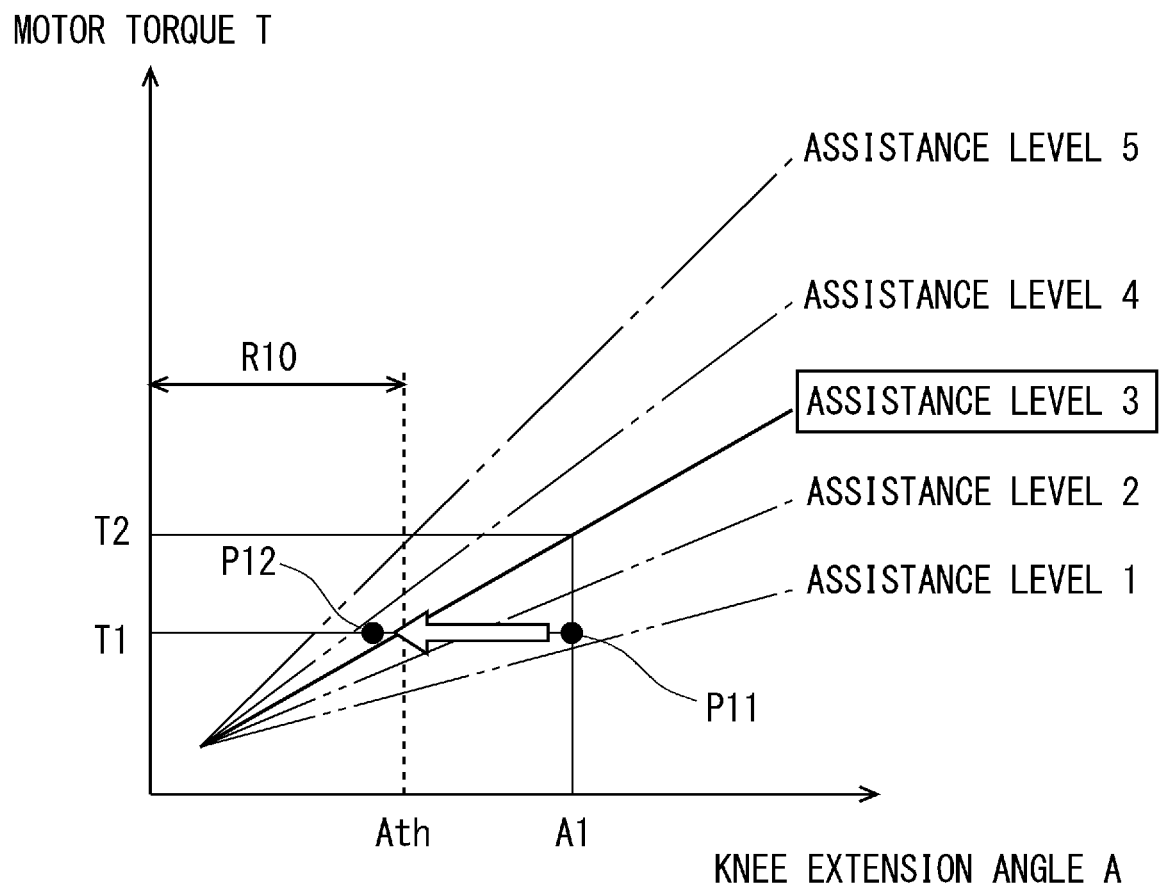
FIG. 7 is a second diagram showing an example of an assistance level.

A specific example of the assistance level will be described with reference to FIG. 7. FIG. 7 is a second diagram showing an example of the assistance level. The graph of FIG. 7 shows a state in which the assistance level 3 is selected at the time of walking training. Further, a point P11 shown in the drawing indicates that the knee extension angle of the diseased leg exceeds the threshold Ath and becomes an angle A1. In this case, the motor 121M assists an extending motion of the trainee 900's knee in such a way that the knee extension angle becomes smaller than the threshold Ath and fall within a range R10. A point P12 shown in the drawing indicates that the knee extension angle of the diseased leg assisted by the motor 121M becomes smaller than the threshold Ath.

A torque T1 shown in the drawing is a torque output by the motor 121M when it actually assists the diseased leg. A torque T2 shown in the drawing is a torque that the motor 121M with a setting of the assistance level 3 can output with the knee extension angle of the angle A1. In the example shown in the drawing, the motor 121M can be driven at the maximum torque T2 at the angle A1. However, it can be seen, from an observation of a transition from the point P11 to the point P12 plotted in the drawing, that the motor 121M can assist with the torque T1 in actuality. When the motor 121M is assisting with a torque lower than the maximum torque T2, this means that the trainee 900 is trying to extend his/her knee using his/her own power. That is, while the angle A1 of the trainee 900's diseased leg transitions within the range R10, a combined force of the trainee 900 and the motor 121M acts on the trainee's joint.

The assistance level of the assist performed by the motor 121M of the control unit 121 is set as described above. The threshold Ath may be a value slightly exceeding 15 degrees, for example, 20 degrees or 25 degrees. The walking training may be performed in such a way that the knee extension angle A falls within the range R10 shown in the drawing. By providing assistance in such a way that the knee extension angle A will not exceed the range R10, the walking training apparatus 100 can provide proper training. Although it is described that there are five assistance levels, there may instead be two or more levels. The above-described threshold Ath may be appropriately changed according to the assist timing.

The assistance level has been described so far. In order to effectively perform walking training using the walking training apparatus 100, it is important to set an appropriate assistance level. For example, when the setting of the assistance level is too high, the trainee 900 depends too much on the assistance of the motor 121M to exert his/her own power. In such a case, the training exercise cannot be effective. However, when the assistance level is set too low, the trainee 900 may not be able to fully extend his/her knee. In this case, the trainee 900's motivation to do the training is lowered, or the possibility of the trainee 900 falling down while walking is increased. In order to prevent such a situation from occurring, the assistance level may be set to a level at which the minimum assistance needed by the trainee 900 to exert his/her own power is needed.

However, when the assistance level is set depending on a training staff member's skill, there is a possibility that a difference between assistance level settings may become greater according to each training staff member. For example, an experienced PT can set the assistance level to an appropriate level as described above. However, a less experienced training staff member may not be able to set the assistance level appropriately, resulting in an ineffective training. Thus, the walking training apparatus 100 according to this embodiment uses the reference data stored in the storage unit 209 to present a recommended assistance level which corresponds to an assistance level employed by an experienced PT to perform training.

Figure 8:
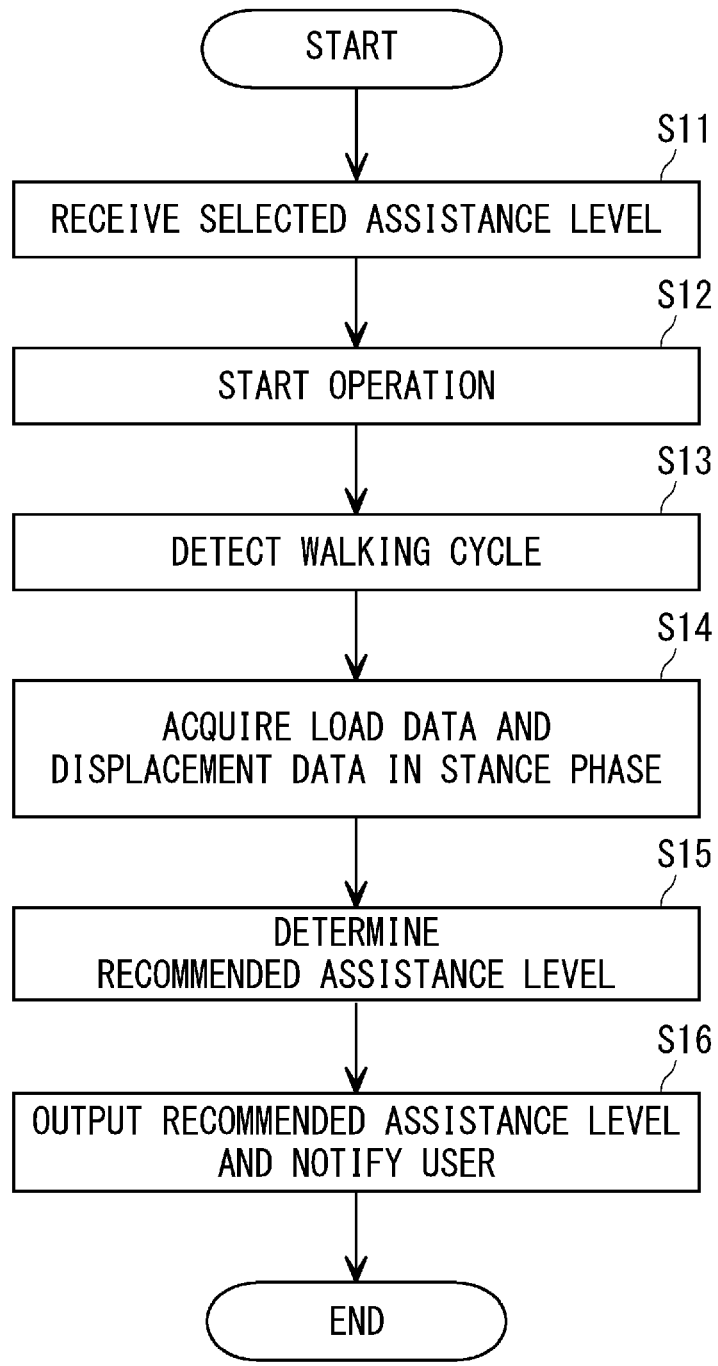
FIG. 8 is a flowchart showing processing of the walking training apparatus according to the first embodiment.

Next, a method in which the walking training apparatus 100 presents a recommended assistance level will be described with reference to FIG. 8. FIG. 8 is a flowchart showing the processing of the walking training apparatus 100 according to the first embodiment. The flowchart shown in FIG. 8 assumes that the trainee 900 attaches the walking assistance apparatus 120 at a predetermined position on the treadmill 131.

First, in order to start walking training, the training staff member 901 such as a PT makes a predetermined setting in the walking training apparatus 100. The predetermined setting includes the setting of the assistance level selected by the training staff member 901. The overall control unit 210 receives the selected assistance level through the operation reception unit 212 (step S11).

Next, the walking training apparatus 100 starts operating by the operation of the training staff member 901 (step S12). When the operation of the walking training apparatus 100 is started, the treadmill 131 is driven, and the trainee 900 starts walking.

Next, the walking cycle detection unit 210b of the overall control unit 210 detects the walking cycle by the method described above (step S13).

Next, the recommended assistance level determination unit 210c acquires the load data and displacement data from the walking assistance apparatus 120 (step S14).

Further, the recommended assistance level determination unit 210c determines a recommended assistance level from the acquired load data and displacement data (step S15).

Next, the overall control unit 210 outputs the determined recommended assistance level to notify the training staff member 901 (step S16). More specifically, the recommended assistance level is displayed on, for example, the training monitor 138 or the management monitor 139. That is, in this case, the training monitor 138 or the management monitor 139 is a notification unit for notifying a user such as the training staff member 901 of the recommended assistance level. Note that means for notifying the user of the recommended assistance level is not limited to this, and instead voice, vibration, or LED light emission may be used.

Figure 9:
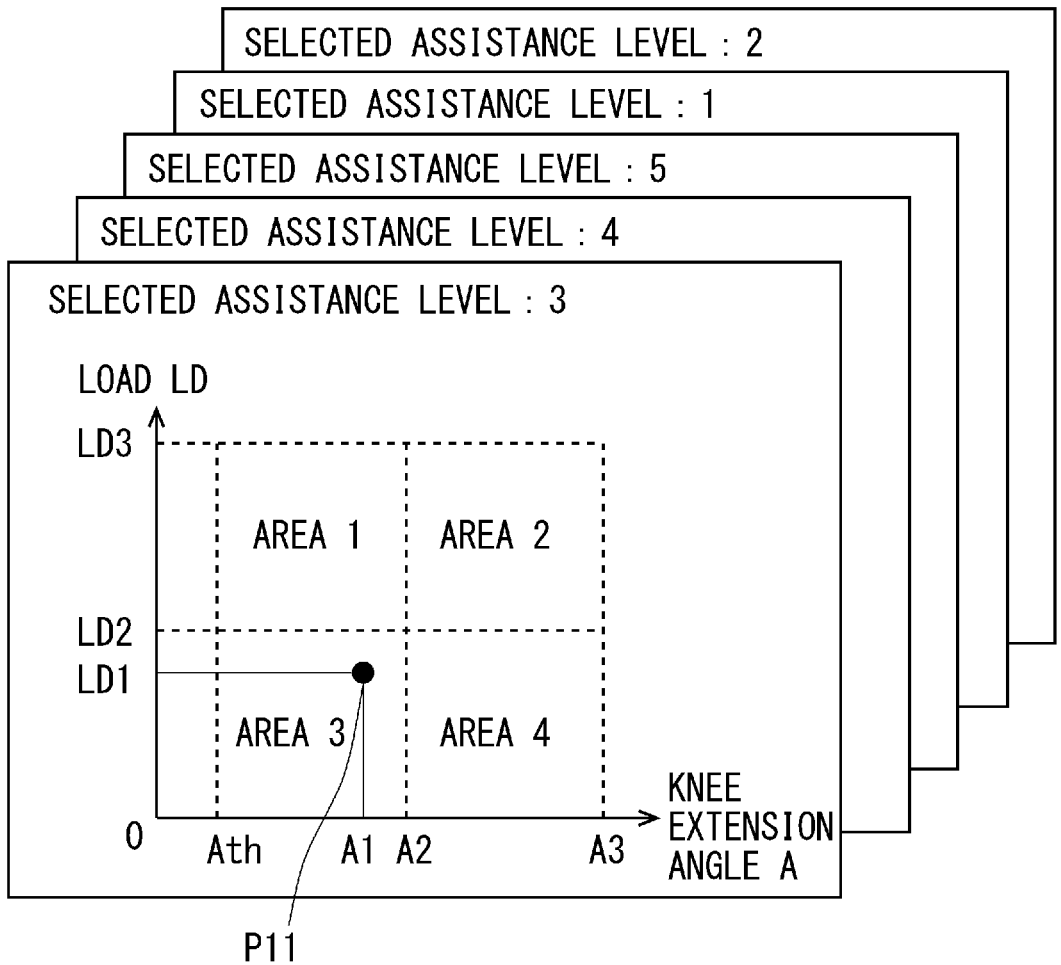
FIG. 9 shows an example of a condition for determining a recommended assistance level according to the first embodiment.

The process of determining the recommended assistance level in step S15 will be described in detail with reference to FIG. 9. FIG. 9 shows an example of a condition for determining the recommended assistance level according to the first embodiment. The graph of FIG. 9 shows the reference data stored in the storage unit 209. In this embodiment, the reference data stored in the storage unit 209 is set for each selected assistance level. Thus, the recommended assistance level determination unit 210c reads the reference data corresponding to the selected assistance level. Here, as a specific example, reference data having a selected assistance level of 3 is shown, assuming that assistance level 3 is selected.

The horizontal axis of the graph shown in FIG. 9 represents the knee extension angle A, and the vertical axis of the graph shown in FIG. 9 represents a load LD of the motor 121M. The threshold value Ath, an angle A2, and an angle A3 are set for the knee extension angle A, and a load LD2 and a load LD3 are set for the load LD. The graph is divided into four areas of areas 1 to 4 using the threshold value Ath, the angle A2, the angle A3, the load LD2, and the second load LD3 as boundaries. The area 1 is in the range of the angles Ath to A2 and loads LD2 to LD3. The area 2 is in the range of the angles A2 to A3 and loads LD2 to LD3. The area 3 is in the range of the angles Ath to A2 and loads 0 to LD2. The area 4 is in the range of the angles A2 to A3 and loads 0 to LD2.

The recommended assistance level determination unit 210c plots the acquired angle data and load data in the reference data. The recommended assistance level determination unit 210c determines a recommended assistance level from an area to which the plotted data belongs.

For example, in the area 1, a relatively large load is applied to the motor 121M within a range of relatively small angles. In this case, the recommended assistance level determination unit 210c determines to maintain the selected assistance level.

In the area 2, a relatively large load is applied to the motor 121M at a relatively large angle. That is, the trainee 900 needs a strong assistance in which the knee extension angle A is larger than that in the walking of a healthy person. Thus, when the acquired data belongs to the area 2, the recommended assistance level determination unit 210c determines to present an assistance level higher than the selected assistance level as the recommended assistance level. For example, when the selected assistance level is 3, the recommended assistance level determination unit 210c determines that the recommended assistance level is 4.

In the area 3, a relatively small load is applied to the motor 121M at a relatively small angle. That is, the trainee 900 walks with the knee extension angle A close to that of a healthy person and with little assistance. Thus, when the acquired data belongs to the area 3, the recommended assistance level determination unit 210c determines to present an assistance level lower than the selected assistance level as the recommended assistance level. For example, when the selected assistance level is 3, the recommended assistance level determination unit 210c determines that the recommended assistance level is 2.

For example, in the area 4, a relatively small load is applied to the motor 121M within a range of a relatively large angle. In this case, the recommended assistance level determination unit 210c determines to maintain the selected assistance level.

As a specific example, a point P11 illustrated in FIG. 7 is shown in the graph of FIG. 9. The point P11 is at the angle A1, load LD1, and belongs to the area 3. Thus, in this case, the recommended assistance level determination unit 210c determines that the recommended assistance level is set to 2.

Figure 10:
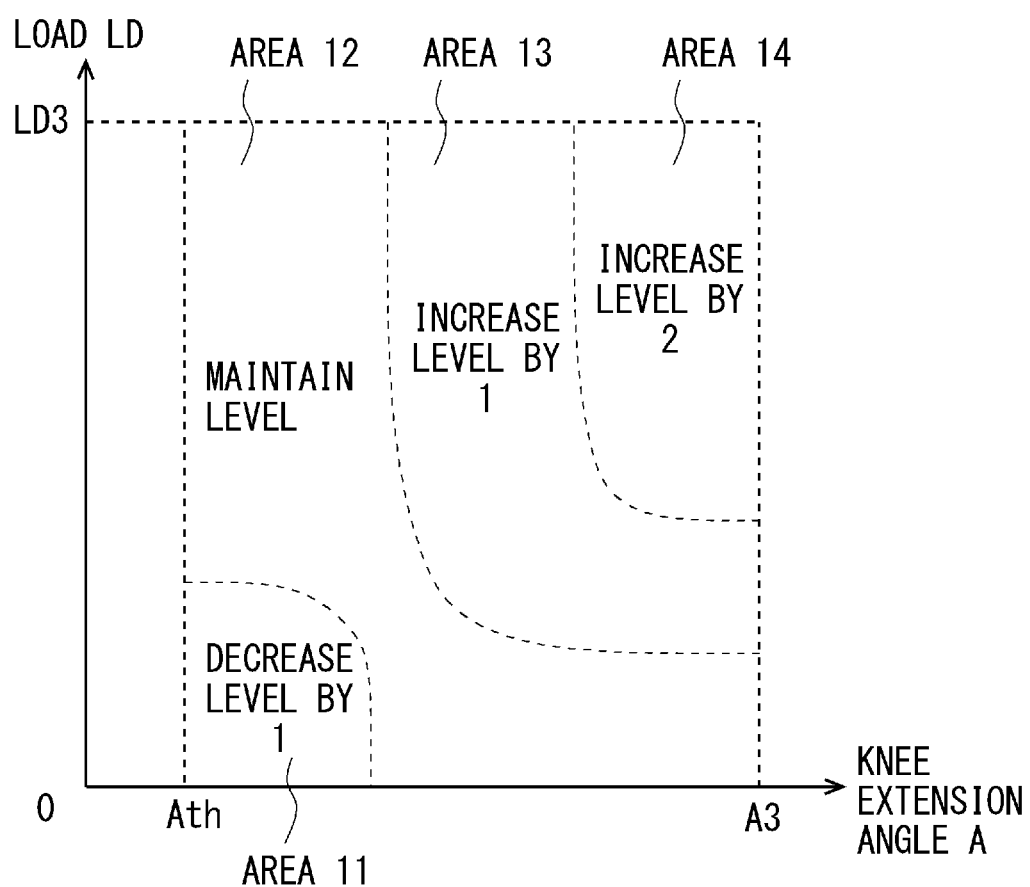
FIG. 10 shows a second example of a condition for determining a recommended assistance level.

Another example of the reference data stored in the storage unit 209 will be described with reference to FIG. 10. FIG. 10 shows a second example of a condition for determining a recommended assistance level. The graph shown in FIG. 10 is reference data at any assistance level. The reference data shown in FIG. 10 differs from the example shown in FIG. 9 in that the reference data of FIG. 10 has areas 11 to 14, and each area has a non-linear area. When the acquired data belongs to the area 14, the recommended assistance level determination unit 210c determines to raise the assistance level by 2 stages. In this way, the reference data can be composed of data of various patterns. The reference data is not limited to the above-described pattern. For example, the reference data does not determine whether the assistance level is relatively changed in the manner described above and instead may determine what level the recommended assistance level should be when the selected assistance level belongs to a predetermined area.

The first embodiment has been described so far. As described above, the walking training apparatus 100 according to the first embodiment can determine a recommended assistance level from the assistance level, the load data, and the output of the displacement sensor acquired from the motions performed by the user. Such a configuration can be applied not only to the above-described walking training apparatus but also to various motion support systems. The walking training apparatus 100 according to the first embodiment may be referred to as a motion support apparatus. The walking training apparatus 100 executes a method for operating the motion support apparatus. The method performed by the walking training apparatus 100 may be executed by hardware and software in cooperation, or may be performed through hardware by software executing a program. Thus, according to the first embodiment, it is possible to provide a motion support system or the like for setting an appropriate assistance level.

Second Embodiment

Figure 11:
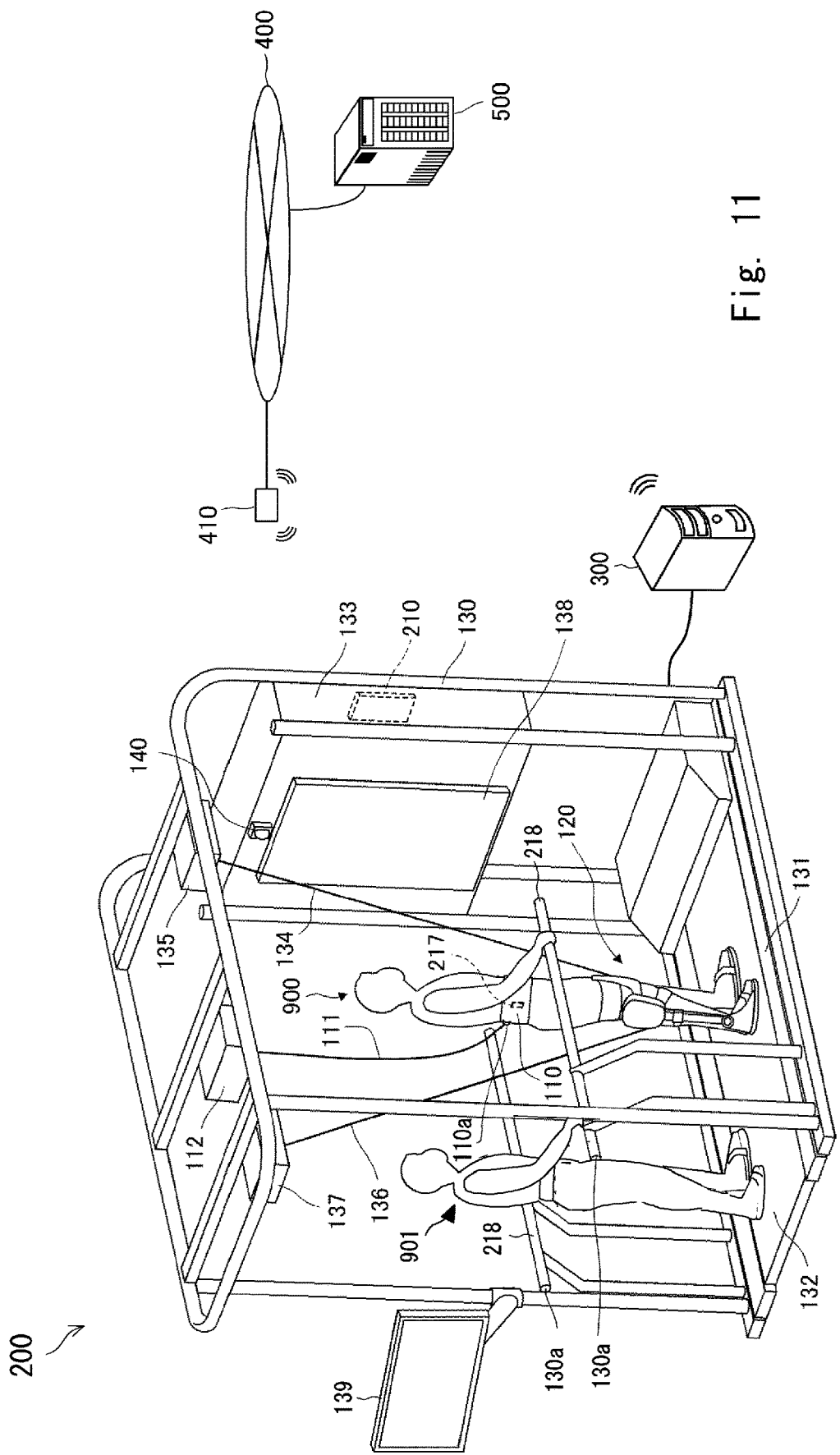
FIG. 11 is a schematic perspective view of a rehabilitation support system according to a second embodiment.

Next, a second embodiment will be described. A rehabilitation support system according to the second embodiment differs from the rehabilitation support system according to the first embodiment in that in the rehabilitation support system according to the second embodiment, a recommended assistance level is determined using a trained model stored in a server connected to the walking training apparatus. FIG. 11 is a general conceptual diagram showing an example of a configuration of the rehabilitation support system according to the second embodiment. The rehabilitation support system (rehabilitation system) according to the second embodiment mainly includes a walking training apparatus 200, an external communication apparatus 300, and a server (server apparatus) 500.

A hardware configuration of the walking training apparatus 200 differs from that of the walking training apparatus 100 according to the first embodiment in that the walking training apparatus 200 is communicably connected to the external communication apparatus 300. Note that a description for the part of the walking training apparatus 200 the same as a corresponding part of the walking training apparatus 100 according to the first embodiment will be omitted.

The external communication apparatus 300 is a specific example of transmission means for transmitting profile data and rehabilitation data to the outside. The external communication apparatus 300 can have a function of receiving and temporarily storing data output from the walking training apparatus 200, and a function of transmitting the stored data to a server 500.

The external communication apparatus 300 is connected to the control panel 133 of the walking training apparatus 200 by, for example, a USB (Universal Serial Bus) cable. The external communication apparatus 300 is connected to a network 400 such as the Internet or an intranet through a wireless communication device 410 by, for example, a wireless LAN (Local Area Network). The walking training apparatus 200 may include a communication apparatus in place of the external communication apparatus 300.

The server 500 is a specific example of information processing means for receiving the profile data and processing the received profile data. The server 500 is connected to the network 400 and has a function of storing the profile data received from the external communication apparatus 300. The functions of the server 500 will be described later.

Figure 12:
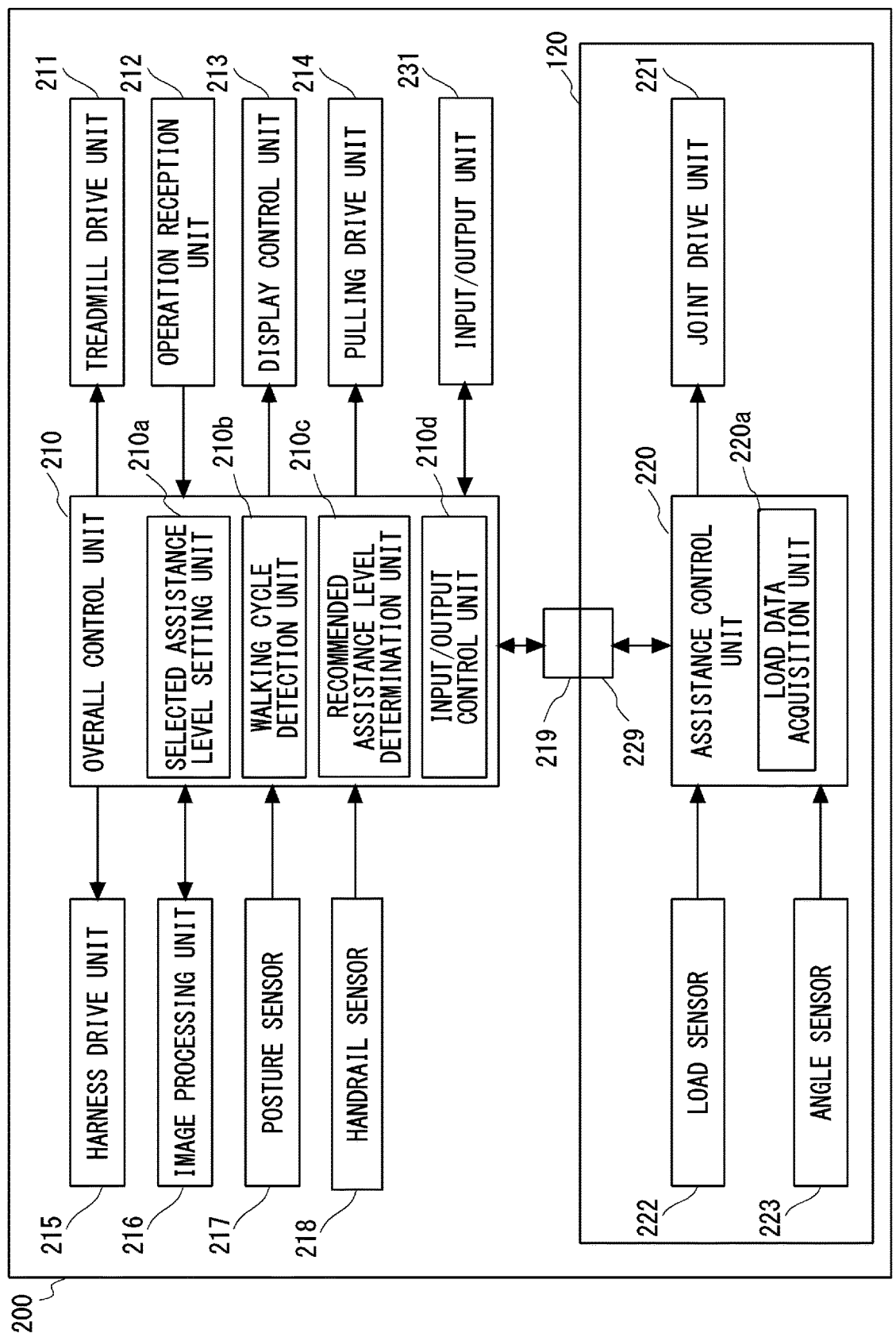
FIG. 12 is a block diagram showing a system configuration of the rehabilitation support system.
Figure 13:
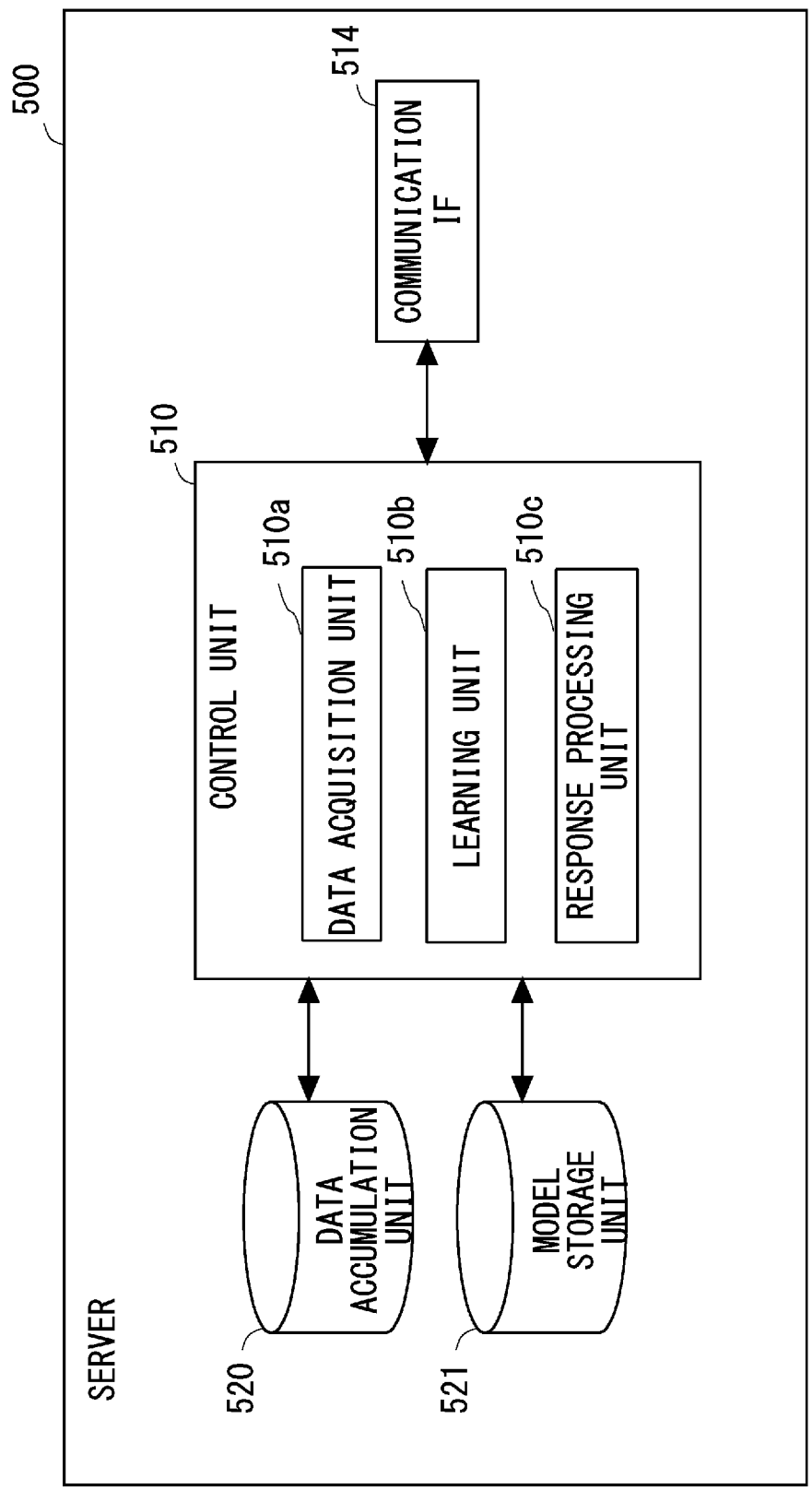
FIG. 13 is a block diagram showing a configuration of a server.

Next, an example of the system configuration of the walking training apparatus 200 will be described with reference to FIG. 12. FIG. 12 is a block diagram showing an example of the system configuration of the walking training apparatus 200. The walking training apparatus 200 differs from the walking training apparatus 100 in that the walking training apparatus 200 includes an input and output unit 231. The walking training apparatus 200 differs from the walking training apparatus 100 in that the walking training apparatus 200 does not include the storage unit 209 for storing the reference data and the recommended assistance level determination unit 210c.

The input and output unit 231 includes, for example, a USB (Universal Serial Bus) interface, and is a communication interface for connecting to an external device (external communication apparatus 300 or other external device). The input and output unit 231 serves functions as an output unit for outputting predetermined data as an input to an external device and as an input unit for receiving predetermined data from the external device.

The input and output control unit 210d of the overall control unit 210 communicates with the external device through the input and output unit 231, rewrites the above-described control program in the overall control unit 210 and a control program in the assistance control unit 220, accepts commands, and outputs predetermined data.

The overall control unit 210 generates temporary assistance data including various information about the trainee when the trainee performs training. The temporary assistance data includes at least load data and displacement data in the stance phase, and further includes profile data of the trainee. The profile data may include, for example, symptom information of a disease that the trainee is suffering from, a cognitive level based on a functional independence measure, an assessment score based on a stroke impairment assessment set, an exercise ability level based on an exercise ability evaluation of the trainee, data indicating the degree of recovery, and data indicating attributes of the trainee.

With the above configuration, the walking training apparatus 200 communicates with the server 500 through the input and output unit 231 and the external communication apparatus 300 under the control of the input and output control unit 210d. For example, the input and output control unit 210d transmits the above temporary assistance data to the server 500 through the input and output unit 231 and the external communication apparatus 300. The input and output control unit 210d performs control to receive the recommended assistance level corresponding to the transmitted temporary assistance data.

Next, the server 500 will be described in detail. The server 500 receives the temporary assistance data from the walking training apparatus 200 through the network 400 and then processes the received temporary assistance data. The server 500 uses a previously stored trained model when processing the temporary assistance data. The trained model is generated by performing machine learning using a plurality of teacher data pieces. The server 500 uses the trained model to determine a recommended assistance level from the received temporary assistance data. The server 500 transmits an assistance level as a processing result to the walking training apparatus 200 through the network 400. The server 500 may be configured to receive a plurality of temporary assistance data pieces from a plurality of walking training apparatuses 200. This allows the server 500 to collect a large amount of temporary assistance data.

FIG. 12 is a block diagram showing an example of a configuration of the server 500. As shown in FIG. 12, the server 500 may include a control unit 510, a communication IF 514, a data accumulation unit 520, and a model storage unit 521. The control unit 510 is, for example, an MPU and controls the server 500 by executing a control program loaded from a system memory. The control unit 510 may include a data acquisition unit 510a, a learning unit 510b, and a response processing unit 510c, which will be described later. Further, in this case, the above-described control program includes a program(s) for implementing the functions of the aforementioned units 510a to 510c.

The communication IF 514 includes, for example, a wired LAN interface and is a communication interface for connecting to the network 400. The control unit 510 can receive temporary assistance data from the walking training apparatus 200 and transmit a processing result to the walking training apparatus 200 through the communication IF 514.

The data accumulation unit 520 includes a storage device such as an HDD (hard disk drive) or an SSD (solid state drive) and stores rehabilitation data therein. The control unit 510 writes the temporary assistance data received from the external communication apparatus 300 into the data accumulation unit 520 through the communication IF 514.

Similarly, the model storage unit 521 includes a storage device such as an HDD or an SSD. Note that the data accumulation unit 520 and the model storage unit 521 may include (i.e., share) a common storage device. When the server 500 performs a rehabilitation support process in cooperation with the walking training apparatus 200, at least an operable trained model is stored in the model storage unit 521.

The server 500 has a function as a learning apparatus for generating a trained model in addition to a function for outputting a recommended assistance level for the temporary assistance data received from the walking training apparatus 200. That is, the control unit 510 may be configured so as to perform control to switch between a function as a learning apparatus and a function for performing a rehabilitation support process by using a trained model. However, the server 500 may be distributed to (or divided into) an apparatus that is used in a learning stage and an apparatus that is used in an operation stage in which a trained model is used.

In the learning stage, the data acquisition unit 510a acquires the temporary assistance data and a selected assistance level that is an assistance level selected corresponding to this temporary assistance data. The data acquisition unit 510a acquires arbitrary temporary assistance data when the rehabilitation support processing is performed.

The learning unit 510b is provided to make the server 500 function as a learning apparatus, and the response processing unit 510c is provided to make the server 500 execute a part of the rehabilitation support processing.

The model storage unit 521 stores at least one of a learning model that has not been trained yet (including those under training) (hereinafter referred to as an untrained model) and a learning model that has been already trained (hereinafter referred to as a trained model). The server 500 serving as the learning apparatus is a processing apparatus for processing various data. For example, the server 500 performs machine learning using the acquired temporary assistance data and teacher data to generate a trained model. The learning apparatus may be referred to as a learning model generating apparatus. When the server 500 functions as a learning apparatus, at least an untrained model is stored in the model storage unit 521.

(Profile Data)

The profile data will be described here. The profile data acquired by the server 500 indicates information about the trainee, and includes at least one of the following types of information (1) to (5).

(1) Symptom Information of Disease that Trainee is Suffering from

Symptom information may include a type(s) of a disease(s) (a name(s) of a disease(s) or a disorder(s)) that the subject has suffered from, such as a stroke (a cerebrovascular disorder) and a spinal cord injury. Further, the symptom information may also include, depending on the type of the disease, its classification. For example, strokes can be classified into cerebral infarction, intracranial hemorrhage (cerebral hemorrhage/subarachnoid hemorrhage), etc. The symptom information may also include information indicating an initial symptom, a time when the symptom appears, and a current symptom in association with the above information. The symptom information may also include symptoms that are unlikely to be directly related to the rehabilitation in addition to the information indicating that the trainee needed to perform rehabilitation because of the symptoms included in the symptom information.

(2) Trainee's Cognitive Level Based on Functional Independence Measure

As a method for evaluating the trainee's cognitive level, for example, FIM (Functional Independence Measure) is known. The FIM (Functional Independence Measure) is one of the evaluation methods for evaluating ADL (Activities of Daily Life). In the FIM, a patient is evaluated (i.e., classified) into seven stages, i.e., one point to seven points according to the level of assistance.

When the cognitive level of the trainee who performs a walking training is evaluated, a walking FIM is a general index indicating the degree of recovery. The walking FIM evaluates the cognitive level into seven stages from one point to seven points. For example, a patient who can walk 50 m or longer without an assistant and without a harness (an assistance apparatus) receives the highest score of seven points. Further, a patient who can walk less than 15 m no matter how much assistance is provided by one assistant receives the lowest score of one point. Further, when a patient can move 50 m with the minimum assistance (an assistance level of 25% or lower), he/she receives four points, whereas when a patient can move 50 m with medium assistance (an assistance level of 25% or higher), he/she receives three points. Therefore, as the recovery progresses, the walking FIM of the trainee gradually increases.

Further, the walking FIM can be regarded as a score that is obtained under the condition at the time of the evaluation, such as when the patient wears the harness. In this case, information indicating the condition applied at the time of the evaluation may be added in the information indicating the walking FIM. The condition may include a condition at the time when the information is acquired, such as a adjusting thickness, a used harness (e.g., with the walking assistance apparatus 120, with other walking assistance apparatuses, without any harness, etc.), a setting such as an angular setting of a part of the knee or the ankle in the harness, and/or whether the walking is performed on a level ground or on a slope. Further, in general, the walking FIM means a walking FIM in walking on a level ground. Further, level-ground walking information indicating such walking FIM may include information such as the longest distance that the patient has walked (the maximum continuous walking distance [m]) in the evaluation of the level-ground walking.

(3) Trainee's Assessment Score Based on Stroke Impairment Assessment Set

There is, for example, SIAS (Stroke Impairment Assessment Set) as an assessment method for quantifying an index for dysfunction caused by a stroke the trainee is suffering from. The SIAS may include a hip flexion test (Hip-Flex), a knee extension test (Knee-Ext), and a foot-pat test (Foot-Pat). Further, the SIAS may also include a lower limb tactile sensation (Touch L/E), a lower limb position sensation (Position L/E), an abdominal muscle strength (Abdominal), and a verticality test (Verticality).

(4) Data Indicating the Trainee's Degree of Recovery

The data indicating a change in the above-described walking FIM (index data) can be data indicating the trainee's degree of recovery. Further, the amount of change from the initial walking FIM to the latest walking FIM or its changing speed is also used as an index indicating the degree of recovery. The change speed may also be referred to as FIM efficiency. For example, the changing speed may be a value that is obtained by dividing the gain (the amount of change) up to the current FIM by, for example, the number of days of the rehabilitation, the number of elapsed days indicating a period of the rehabilitation, or the number of days the patient has been hospitalized in the case where the trainee is a hospitalized patient.

The data indicating the trainee's degree of recovery may be the Br. stage (Brunnstrom Recovery Stage). The Br. stage is an indicator of recovery in which a recovery process of a hemiplegia is divided into six stages based on the observation. In this embodiment, the data indicating the trainee's degree of recovery may include, of the Br. stage, lower-limb items that are main items related to the walking training apparatus 200.

(5) Data Indicating Attributes of the Trainee

The data indicating attributes of the trainee include, for example, the trainee's age, sex, physique (height, weight, etc.), and a score indicating the trainee's physical condition.

Although the profile data has been described in detail above, the profile data is not limited to the above-described items. The profile data may include information of types different from those described above as long as it includes information satisfying the purpose of the profile data. The profile data may also include additional information such as a date and a time when the data is measured.

(Learning Stage)

Figure 14:
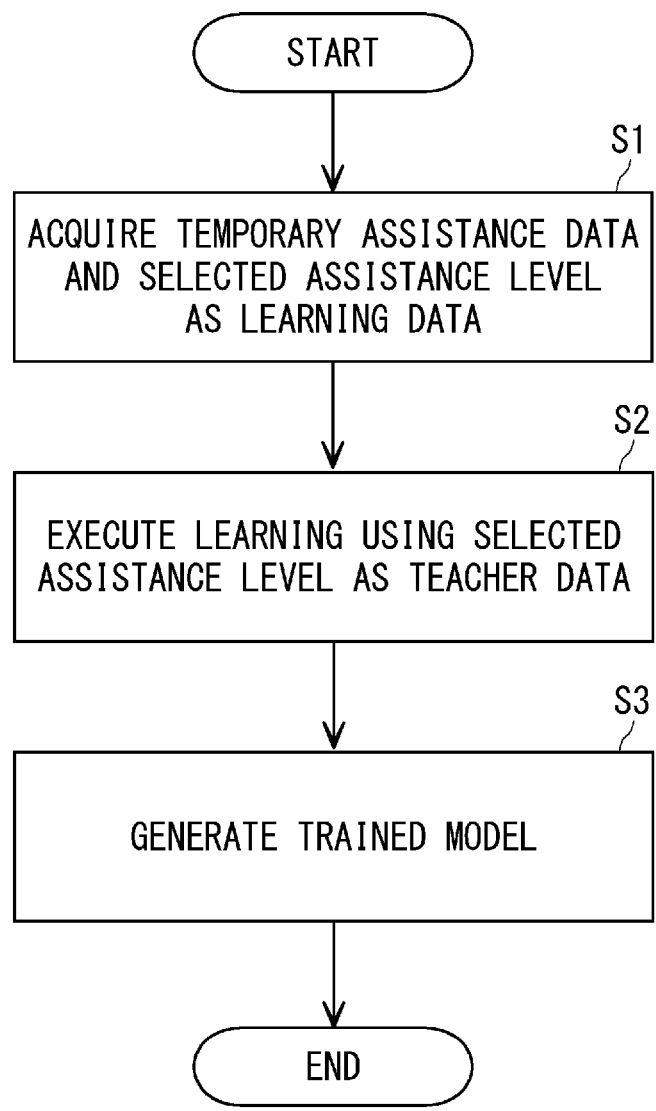
FIG. 14 is a flowchart showing processing for generating a trained model according to the second embodiment.

Next, the processing in the learning stage performed by the server 500 as the learning apparatus will be described with reference to FIG. 14. FIG. 14 is a flowchart for describing processing in the server 500, which is a learning apparatus.

First, the data acquisition unit 510*a* of the server 500 acquires the temporary assistance data and the selected assistance level as learning data (step S1). That is, when the server 500 performs learning, the selected assistance level corresponding to the temporary assistance data and the acquired temporary assistance data becomes one set of learning data.

As described above, the temporary assistance data includes at least one of the following data: symptom information of the disease that the trainee is suffering from; a cognitive level based on the functional independence measure; an assessment score based on the stroke impairment assessment set; an exercise ability level based on the exercise ability evaluation; information indicating the degree of recovery; and attribute data of the trainee. The selected assistance level is an assistance level selected in the training performed corresponding to the acquired profile data. The selected assistance level acquired by the server 500 is selected when the experienced PT configures an effective training.

Next, the learning unit 510*b* of the server 500 applies the acquired temporary assistance data to an input layer, and executes learning with the corresponding selected assistance level as the teacher data (step S2).

FIG. 15 is a table showing an example of data input to the learning apparatus. In the table shown in the drawing, the numbers in the left column are data set numbers (1,2, 3 . . . ). The column to the right of the data set number is the data (2, 1, 7 . . . ) of the walking FIM as a parameter 1 applied to the input layer. The column to the right of the walking FIM is SIAS data (3, 2, 6 . . . ) as a parameter 2. The column to the right of SIAS is displacement data (data 13, 23, 33 . . . ) corresponding to the knee extension angle as a parameter 3. The column to the right of the displacement data is load data (data 14, 24, 34 . . . ) as a parameter 4. The column to the right of the load data indicates the assistance level (2, 5, 1 . . . ) as the teacher data.

As described above, the data input to the learning apparatus includes a plurality of parameters applied to the input layer and the teacher data applied to the output layer. By performing the learning using such a plurality of data sets, the server 500, which is a learning apparatus, causes the learning unit 510*b* to learn. By using the above-mentioned learning data, the learning unit 510*b* learns to determine the recommended assistance level, which is the assistance level of the assistance apparatus recommended to be selected when the trainee uses the rehabilitation support apparatus.

Note that the type of the learning model to be trained and its algorithm are not limited to any particular types and algorithms. However, a neural network can be used as the algorithm and, in particular, a deep neural network (DNN) using multiple hidden layers may be used. As the DNN, for example, a feedforward (forward propagation type) neural network such as a multilayer perceptron (MLP) employing an error back propagation method can be used.

Examples of input parameters input to the untrained model in the learning unit 510*b* and output parameters output from the untrained model will be described hereinafter by using an example in which the learning unit 510*b* generates a trained model by using the MLP. Each of the input parameters corresponds to a respective one of nodes in the input layer and each of the output parameters corresponds to a respective one of nodes in the output layer (i.e., objective variables). Note that an untrained model (untrained learning model) includes not only a completely untrained model but also a model under a learning process.

Figure 16:
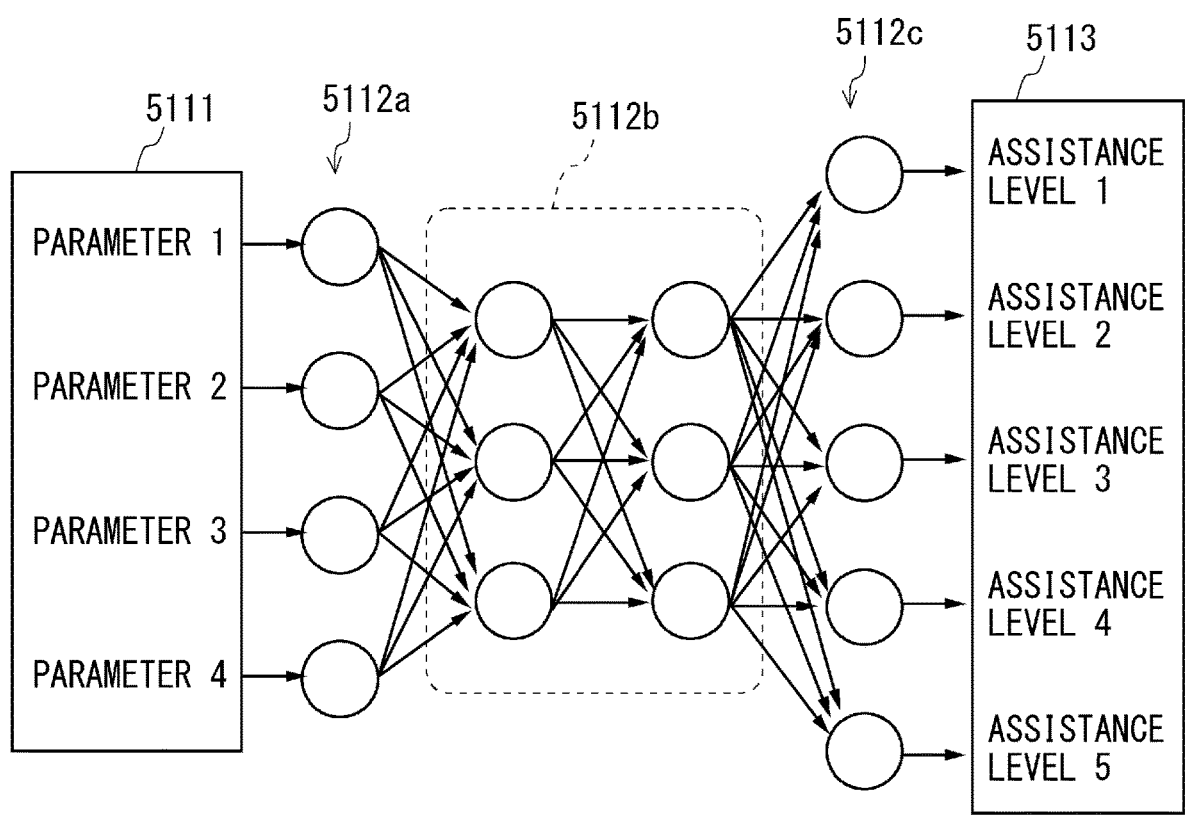
FIG. 16 shows an example of a learning model.

FIG. 16 shows an example of a learning model. FIG. 16 shows a learning model 5110. The learning model 5110 includes an input layer 5112*a*, an intermediate layer 5112*b* (also referred to as a hidden layer), and an output layer 5112*c*. The intermediate layer 5112*b* is provided between the input layer 5112*a* and the output layer 5112*c*.

The input layer 5112*a* includes a plurality of nodes, and receives data included in the data set. The intermediate layer 5112*b* includes a plurality of nodes. Note that the number of nodes and the number of hidden layers in the intermediate layer shown in the drawing are only examples, and the number of nodes and the number of layers are not limited to those shown in the drawing.

The output layer 5112*c* outputs a value for determining the recommended assistance level. In this embodiment, the output layer includes 5 nodes respectively corresponding to the assistance levels 1 to 5. When an objective function 5111 is input, the learning model 5110 outputs a predetermined numerical value to the output layer 5112c. The output of the output layer 5112c is compared with the teacher data 5113, and a result of the comparison is fed back. The learning model 5110 updates the threshold, weighting and the like in the learning model by repeating this processing.

Next, the learning unit 510b generates a trained model updated by the performed learning (step S3). The trained model indicates a learning model at a stage where the learning model updated by the above processing becomes operable.

By the above processing, the server 500 as the learning apparatus generates a trained model for outputting the recommended assistance level. Then, the rehabilitation support system can present a recommended assistance level when walking training is performed by using the generated trained model.

The learning unit 510b may use a neural network having a recursive structure such as RNN (Recurrent Neural Network) as the learning model in addition to the above-described configuration. The RNN may also be a neural network (sometimes simply referred to as LSTM) extended to include LSTM (Long short-term memory) blocks. In addition to the above configuration, the learning unit 510b may use a k-nearest neighbor algorithm (kNN).

(Operation Stage)

Figure 17:
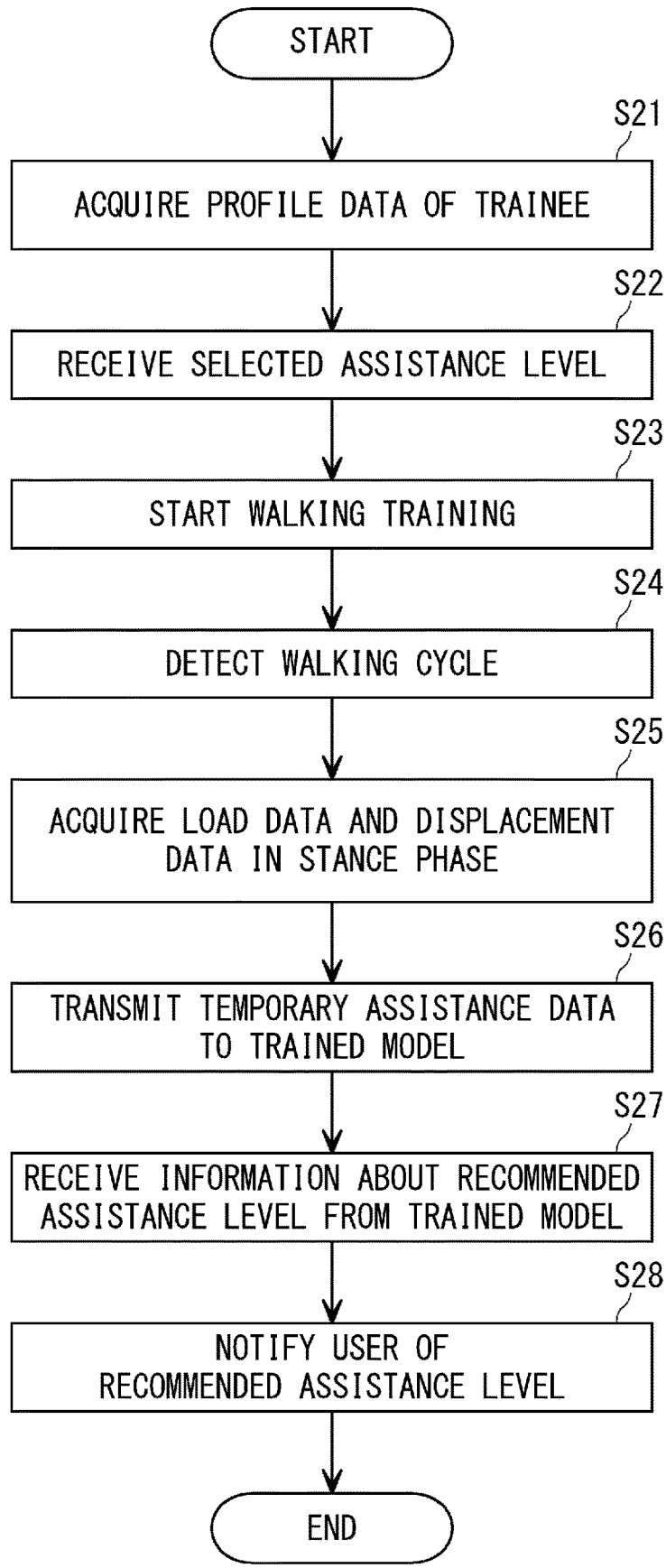
FIG. 17 is a flowchart showing processing of the walking training apparatus according to the second embodiment.

Next, processing performed by the walking training apparatus 200 in the operation stage will be described with reference to FIG. 17. An operation stage is a stage in which rehabilitation is performed using the trained model generated by the learning apparatus. FIG. 17 is a flowchart for explaining an example of the processing of the server. As described above, the walking training apparatus 200 can use the trained model by accessing the server 500. At the operation stage, mainly the walking training apparatus 200 and the server 500 connected to the walking training apparatus through a network cooperate with each other as a rehabilitation support system, and rehabilitation support processing is performed.

First, the walking training apparatus 200 acquires profile data of a trainee (step S21). More specifically, the walking training apparatus 200 receives the profile data input by a PT or the like. The input of the profile data by the PT or the like is achieved, for example, by the overall control unit 210 controlling the display control unit 213 to cooperate with the operation reception unit 212.

Next, the walking training apparatus 200 receives the selected assistance level (step S22). The selected assistance level is determined by, for example, a PT. When the PT determines the selected assistance level, the PT may, for example, refer to the data of the walking training performed previously by the trainee 900 or may select the assistance level employed in the walking training performed by another trainee having a cognitive level about the same level as that of the trainee. The PT sets the determined assistance level in the walking training apparatus 200 in order to start training according to the determined assistance level.

Next, the walking training apparatus 200 starts walking training by receiving a predetermined operation (step S23). More specifically, the PT sets various parameters including the assistance level for the walking training apparatus 200, and inputs information about the trainee 900 and information about the PT himself/herself. Additionally, the PT makes preparation such as making the trainee 900 wear the walking assistance apparatus 120. When these settings and preparations are completed, the PT starts walking training by a predetermined operation.

Next, the walking training apparatus 200 detects a walking cycle of the trainee 900 who has started the training (step S24). Further, the walking training apparatus 200 acquires load data and displacement data in the stance phase from the detected walking cycle (step S25).

Next, the walking training apparatus 200 generates temporary assistance data to be input to the trained model from the acquired data, and transmits the generated temporary assistance data to the trained model (step S26). The trained model included in the server 500 receives the temporary assistance data transmitted from the walking training apparatus 200 and outputs the recommended assistance level.

Next, the walking training apparatus 200 receives information about the recommended assistance level from the trained model (step S27). When the walking training apparatus 200 receives the information about the recommended assistance level, it processes the information about the received recommended assistance level and notifies the user of the recommended assistance level (step S28). More specifically, for example, the walking training apparatus 200 displays the recommended assistance level on the management monitor 139. The PT notified of the recommended assistance level applies the recommended assistance level to the walking training in the subsequent training.

By such processing, the walking training apparatus 200 can display the recommended assistance level corresponding to the received profile data and the selected assistance level. The PT can set the displayed recommended assistance level as an assistance level to be applied by the walking assistance apparatus 120. With such a configuration, the walking training apparatus 200 can appropriately set the assistance level regardless of the experience or intuition of the PT.

Note that the learning apparatus and the rehabilitation support system described above can be applied to a system for performing an assistance operation of the ankle or hip joint of the trainee in place of or in addition to the assist operation of the knee joint of the trainee. The learning apparatus and the rehabilitation support system described above can also be applied to a rehabilitation support system for training the movement of the arm instead of walking training.

The above-described program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (Read Only Memory), CD-R, CD-R/W, and semiconductor memories (such as mask ROM, PROM (Programmable ROM), EPROM (Erasable PROM), flash ROM, RAM (Random Access Memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

Note that the present disclosure is not limited to the above-described embodiments, and may be appropriately modified without departing from the scope of the present disclosure. For example, the walking training apparatus 100 according to the first embodiment may further include a server communicatively connected thereto, and the server may perform a process for determining a recommended assistance level. In the second embodiment, the walking training apparatus 200 may be connected the server 500 without using the network 400. In this case, in the rehabilitation support system according to the second embodiment, the walking training apparatus 200 and the trained model may be configured as one apparatus.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A motion support system comprising:
    an assistance apparatus configured to assist an extending motion and a flexing motion of a knee joint performed by a user during a walking motion, the assistance apparatus comprising a driving motor;
    a displacement sensor configured to detect a displacement of the knee joint and an angle of the knee joint; and
    a micro processing unit configured to:
    set a selected assistance level, the selected assistance level being an assistance level to be exerted by the assistance apparatus;
    acquire load data regarding a load of the assistance apparatus;
    determine, based on the selected assistance level, the load data, and an output of the displacement sensor, a recommended assistance level that is the assistance level to be recommended, and to output information about the determined recommended assistance level; and
    detect a walking cycle of the walking motion of the user, and when a knee extension angle of the user exceeds a threshold angle during a stance phase of the walking cycle, drive the driving motor to assist the extending motion and the flexing motion of the knee joint with a motor torque determined by the recommended assistance level.

2. The motion support system according to claim 1, further comprising:
    A non-volatile memory configured to store statistical data about a motion of the knee joint performed in the past, the statistical data being generated by collecting the assistance level, the load data, and the output of the displacement sensor, and
    the micro processing unit is configured to determine the recommended assistance level based on the statistical data.

3. The motion support system according to claim 1, wherein
    the motion of the knee joint assisted by the assistance apparatus is included in rehabilitation performed by the user as a trainee,
    the motion support system further comprises a non-volatile memory configured to store statistical data about rehabilitation performed in the past, the statistical data being generated by collecting index data indicating a degree of recovery of the trainee, the assistance level, the load data, and the output of the displacement sensor, and
    the micro processing unit is configured to determine the recommended assistance level based on the statistical data and the index data of the trainee.

4. The motion support system according to claim 1, wherein
    the micro processing unit is configured to acquire information about power consumption of the driving motor.

5. A motion support method executed by a motion support system including an assistance apparatus for assisting an extending motion and a flexing motion of a knee joint performed by a user during a walking motion, the assistance apparatus comprising a driving motor, the motion support method comprising:
    detecting a displacement of the knee joint and an angle of the knee joint;
    setting an assistance level, the assistance level being an assistance level to be exerted by the assistance apparatus;
    acquiring load data regarding a load of the assistance apparatus;
    determining a recommended assistance level that is the assistance level to be recommended based on the assistance level, the load data, and the displacement;
    outputting information about the recommended assistance level; and
    detecting a walking cycle of the walking motion of the user, and when a knee extension angle of the user exceeds a threshold angle during a stance phase of the walking cycle, driving the driving motor to assist the extending motion and the flexing motion of the knee joint with a motor torque determined by the recommended assistance level.

6. A non-transitory computer readable medium storing a program for causing a computer to execute a motion support method executed by a motion support system including an assistance apparatus for assisting an extending motion and a flexing motion of a knee joint performed by a user during a walking motion, the assistance apparatus comprising a driving motor, the motion support method comprising:
    detecting a displacement of the knee joint and an angle of the knee joint;
    setting an assistance level, the assistance level being an assistance level to be exerted by the assistance apparatus;
    acquiring load data regarding a load of the assistance apparatus;
    determining a recommended assistance level that is the assistance level to be recommended based on the assistance level, the load data, and the displacement;
    outputting information about the recommended assistance level; and
    detecting a walking cycle of the walking motion of the user, and when a knee extension angle of the user exceeds a threshold angle during a stance phase of the walking cycle, driving the driving motor to assist the extending motion and the flexing motion of the knee joint with a motor torque determined by the recommended assistance level.

* * * * *